(12) United States Patent
Harvey

(10) Patent No.: US 10,113,130 B1
(45) Date of Patent: Oct. 30, 2018

(54) HIGH DENSITY/HIGH CETANE RENEWABLE FUEL BLENDS

(71) Applicant: The United States of America, as represented by the Secretary of the Navy, Washington, DC (US)

(72) Inventor: Benjamin G Harvey, Ridgecrest, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/055,804

(22) Filed: Feb. 29, 2016

Related U.S. Application Data

(63) Continuation-in-part of application No. 13/951,040, filed on Jul. 25, 2013, now abandoned, and a
(Continued)

(51) Int. Cl.
*C07C 1/20* (2006.01)
*C10L 10/12* (2006.01)
(Continued)

(52) U.S. Cl.
CPC .............. *C10L 10/12* (2013.01); *C07C 1/20* (2013.01); *C07C 1/2078* (2013.01); *C07C 2/02* (2013.01);
(Continued)

(58) Field of Classification Search
CPC .. C10L 1/1608; C10L 1/04; C10L 2200/0469; C10L 2270/026; C10L 2270/04
(Continued)

(56) References Cited

U.S. PATENT DOCUMENTS 4,670,041 A * 6/1987 Payne ................... A01N 43/90
504/235
4,670,620 A 6/1987 Jacobs et al.
(Continued)

FOREIGN PATENT DOCUMENTS

WO WO 2010066830 A1 6/2010

OTHER PUBLICATIONS

Harvey, B.G.; Merriman, W.W.; Koontz, T.A. "High-Density Renewable Diesel and Jet Fuels Prepared from Multicyclic Sesquiterpanes and a 1-Hexene-Derived Synthetic Paraffinic Kerosene", Energy Fuels (Published Feb. 20, 2015); 29, pp. 2431-2436.*
(Continued)

*Primary Examiner* — Philip Y Louie
*Assistant Examiner* — Aaron W Pierpont
(74) *Attorney, Agent, or Firm* — Charlene A. Haley

(57) ABSTRACT

High density renewable diesel and jet fuels have been generated by blending multicyclic sesquiterpanes with a synthetic paraffinic kerosene (5-methylundecane). The sesquiterpanes impart high density and volumetric net heat of combustion to the blends, while inclusion of the modestly branched paraffin decreases the viscosity and increases the cetane number of the blends. A surrogate diesel fuel including 65% sesquiterpanes and 35% 5-methylundecane had a cetane number of 45.7, a density of 0.853 g/ml, and a volumetric net heat of combustion (NHOC) of 133,593 btu/gal. By increasing the amount of paraffin to 60% by volume, a jet fuel surrogate was prepared with a cetane number of 57.0, a density of 0.806 g/ml, a −20° C. viscosity of 7.9 cst, and a NHOC of 124,257 btu/gal. The results show that full-performance and even ultra-performance fuels can be generated by combining bio-derived sesquiterpanes and paraffins.

10 Claims, 7 Drawing Sheets

Related U.S. Application Data continuation-in-part of application No. 14/919,114, filed on Oct. 21, 2015, now Pat. No. 10,053,643, which is a continuation-in-part of application No. 13/676,541, filed on Nov. 14, 2012, now Pat. No. 9,994,498, application No. 15/055,804, which is a continuation-in-part of application No. 14/919,446, filed on Oct. 21, 2015, which is a continuation-in-part of application No. 13/676,541, filed on Nov. 14, 2012, now Pat. No. 9,994,498, application No. 15/055,804, which is a continuation-in-part of application No. 14/919,503, filed on Oct. 21, 2015, which is a continuation-in-part of application No. 13/676,541, filed on Nov. 14, 2012, now Pat. No. 9,994,498, application No. 15/055,804, which is a continuation-in-part of application No. 14/919,529, filed on Oct. 21, 2015, which is a continuation-in-part of application No. 13/676,541, filed on Nov. 14, 2012, now Pat. No. 9,994,498, application No. 15/055,804, which is a continuation-in-part of application No. 14/919,570, filed on Oct. 21, 2015, which is a continuation-in-part of application No. 13/676,541, filed on Nov. 14, 2012, now Pat. No. 9,994,498.

(60) Provisional application No. 61/676,203, filed on Jul. 26, 2012, provisional application No. 61/562,681, filed on Nov. 22, 2011.

(51) Int. Cl.
*C10G 2/00* (2006.01)
*C10L 1/08* (2006.01)
*C07C 1/207* (2006.01)
*C07C 4/02* (2006.01)
*C07C 2/06* (2006.01)
*C07C 2/02* (2006.01)
*C07C 5/31* (2006.01)

(52) U.S. Cl.
CPC .................. *C07C 2/06* (2013.01); *C07C 4/02* (2013.01); *C07C 5/31* (2013.01); *C10G 2/32* (2013.01); *C10L 1/08* (2013.01); *C10L 2200/0469* (2013.01); *C10L 2270/026* (2013.01); *C10L 2270/04* (2013.01); *C10L 2290/42* (2013.01); *C10L 2290/543* (2013.01)

(58) Field of Classification Search
USPC .......................................................... 585/14
See application file for complete search history.

(56) References Cited

U.S. PATENT DOCUMENTS

| | | | | |
|---|---|---|---|---|
| 4,804,795 A | * | 2/1989 | Yuasa | C10L 1/04 252/73 |
| 4,812,224 A | | 3/1989 | Miller | |
| 5,883,057 A | * | 3/1999 | Roell, Jr. | C10M 143/00 508/469 |
| 6,150,575 A | * | 11/2000 | Angevine | C10L 1/08 44/300 |
| 9,109,175 B2 | | 8/2015 | Lee et al. | |
| 2002/0035029 A1 | | 3/2002 | Yoshida et al. | |
| 2003/0013623 A1 | | 1/2003 | Tse et al. | |
| 2008/0071125 A1 | * | 3/2008 | Li | C10L 1/026 585/361 |
| 2008/0092829 A1 | | 4/2008 | Renninger et al. | |
| 2008/0302001 A1 | * | 12/2008 | Koivusalmi | C10G 45/62 44/308 |
| 2009/0013590 A1 | * | 1/2009 | Lamprecht | C10G 2/00 44/436 |
| 2009/0020089 A1 | | 1/2009 | Ryder et al. | |
| 2009/0020090 A1 | | 1/2009 | Ryder et al. | |
| 2009/0036725 A1 | | 2/2009 | Wu et al. | |
| 2009/0070858 A1 | | 3/2009 | Hiraide et al. | |
| 2009/0272119 A1 | | 11/2009 | Ryder | |
| 2009/0272352 A1 | | 11/2009 | Ryder | |
| 2010/0281845 A1 | * | 11/2010 | Renninger | C10L 1/04 60/39.461 |
| 2011/0113679 A1 | | 5/2011 | Cohen et al. | |
| 2011/0288352 A1 | * | 11/2011 | Peters | C10G 3/42 585/14 |
| 2012/0059205 A1 | * | 3/2012 | Rusek | B01J 37/03 585/302 |
| 2012/0101317 A1 | * | 4/2012 | Knight | C10G 1/02 585/21 |
| 2012/0116138 A1 | | 5/2012 | Goodall et al. | |
| 2012/0151828 A1 | * | 6/2012 | Kalnes | C10L 1/00 44/308 |
| 2013/0102817 A1 | * | 4/2013 | Dahlstrom | C10L 1/04 585/13 |

OTHER PUBLICATIONS

Qin, X.; Cao, X.; Guo, Y.; Xu, L.; Hu, S.; Fang, W. "Density, Viscosity, Surface Tension, and Refractive Index for Binary Mixtures of 1,3-Dimethyladamantane with Four C10 Alkanes", J. Chem. Eng. Data. (2014), 59, pp. 775-783.*
Knezevic, D. "Mathematical Modeling of Changing of Dynamic Viscosity, as a Function of Temperature and Pressure, of Mineral Oils for Hydraulic Systems", Mechanical Engineering, 4 (2006), pp. 27-34.*
Bruno, T.J., et. al. "Comparison of Synthetic Isoparaffinic Kerosene Turbine Fuels with the Composition-Explicit Distillation Curve Method" Energy Fuels (2010), 24, pp. 3049-3059.*
Harvey, B.J. et. al. "High-Density Renewable Diesel and Jet Fuels Prepared from Multicyclic Sesquiterpanes and a 1-hexene-derived Synthetic Paraffinic Kerosene"; Energy & Fuels; (2015), 29, pp. 2431-2436. (Year: 2015).*
Kissin, Y.V. "Detailed Kinetics w/1-Hexene Oligom'n React'n w/(n-Bu-Cp) 2ZrCl2-MAO Catalyst", Macro. Chem. and Physics (2009), 210, pp. 1241-1246.
Liu, et al. "Oligomer'n of 1-hexene w/bimetallic cata. based on titanium/zirconium derivatives & organoaluminum cmpds", Polymer Bull. 24, 1990, pp. 355-362.
Anslyn, E. V.; Dougherty, D.A."Modern Physical Organic Chemistry", University Science Books: 2006; p. 796.

* cited by examiner

HIGH DENSITY/HIGH CETANE RENEWABLE FUEL BLENDS

CROSS-REFERENCE TO RELATED APPLICATIONS

This is a continuation-in-part patent application, claiming the benefit of, parent application Ser. No. 13/951040 filed on Jul. 25, 2013, which claims the benefit of, parent application Ser. No. 61/676203 filed on Jul. 26, 2012, and a continuation-in-part patent application, claiming the benefit of, parent applications Ser. No. 14/919114 filed on Oct. 21, 2015, Ser. No. 14/919446 filed on Oct. 21, 2015, Ser. No. 14/919503 filed on Oct. 21, 2015, Ser. No. 14/919529 filed on Oct, 21, 2015, Ser. No. 14/919570 filed on Oct. 21, 2015, all of which are continuation-in-part patent applications, claiming the benefit of, parent application Ser. No. 13/676541 filed on Nov. 14, 2012, which claims the benefit of, parent application Ser. No. 61/562,681 filed on Nov. 22, 2011, which is incorporated hereby reference in its entirety.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods for the preparation of renewable fuel blends that have both high density and high cetane numbers. These fuels will reduce the carbon footprint of the Navy while increasing the range and/or loiter time of a variety of Navy platforms. The high cetane number of these fuels allows for their direct use in diesel engines.

Figure 1:
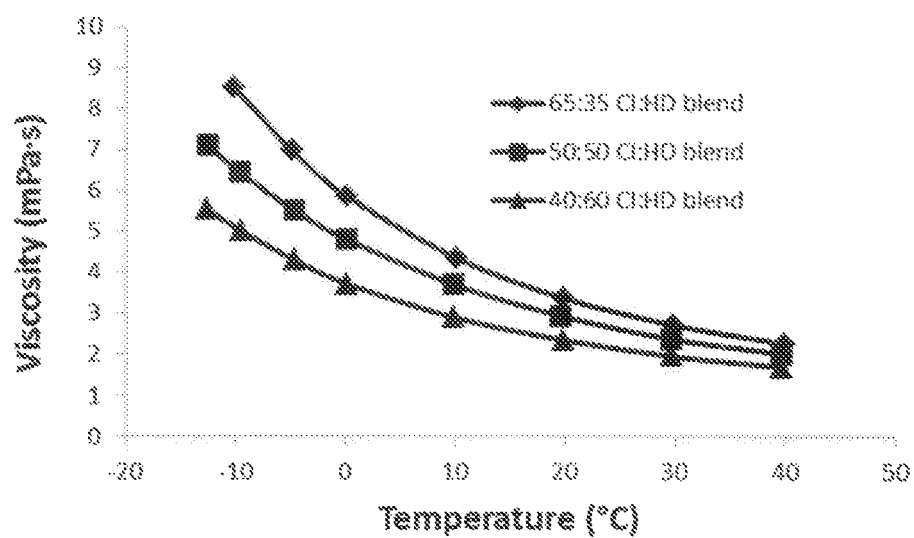
FIG. 1 is a graph illustrating the low temperature viscosities of the fuel blends and measured between −14° C. and 40° C., according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Ethanol is the most widely produced biofuel in the world, with global production estimated at 73 billion gallons per year in 2030. Ethanol is primarily blended with gasoline due to its impressive octane number, but is unsuitable for use in military jet fuel due to its low density and net heat of combustion coupled with its relatively high corrosivity and miscibility with water. Ethanol can be readily dehydrated to the molecule ethylene by reaction with an acidic catalyst at elevated temperature. Oligomerization of ethylene produces linear molecules which have utility as diesel and jet fuels, however conventional approaches produce straight chain molecules that have relatively high melting points and limit the amount of these molecules that can be blended with conventional jet fuels. In contrast, the current approach selectively converts ethylene to 1-hexene which is then oligomerized with a Ziegler Natta catalyst to dimers and trimers, C12 and C18 molecules respectively. Due to the catalyst utilized for the oligomerization, these products have well-defined chain branching which greatly reduces the freezing point of the fuels, but due to the length of the chain, does not adversely affect the cetane number of the fuels. Therefore, fuels produced in this manner are suitable for both jet and diesel propulsion.

The oligomerization of ethylene to produce gasoline range fuel(s) is described in: Amin N. A. S. and Anggoro D. D. J. Nat Gas Chem 11:79-86 (2002). A process for the conversion of bioethanol to polyethylene is described in: Morschbacker A Polym Rev 49:79-84 (2009). A process for the conversion of bioethanol/biobutanol to low density polyethylene is described in: Morschbacker, A and de Castro, L. R. WIPO Patent WO 2009/070858 (2009). 1-hexene dimerization/oligomerization with an unselective heterogeneous catalyst is described in: U.S. Patent No. 6,737,555.

Embodiments of the invention describe a three step method for the conversion of ethanol into fuels that can be utilized as full-performance military jet or diesel fuels. Embodiments of the invention further describe methods for the selective conversion of ethanol to full performance saturated hydrocarbon fuels that are suitable for both jet and diesel propulsion. These sustainable fuels can be produced domestically from biomass and will help the Navy to meet its goals of reducing petroleum usage while reducing greenhouse gas emissions.

1. Ethanol generated from either a renewable source (i.e. sugars, cellulosic or lignocellulosic feedstocks, $CO_2$, bio-derived syngas) or a petrochemical source is dehydrated by use of a heterogeneous catalyst (e.g. alumina) to produce ethylene.

2. Ethylene is selectively converted to 1-hexene by reaction with an ethylene trimerization catalyst (Ti, Cr, Ta, or Zr-based).

3. 1-hexene is converted to a mixture of dimers and trimers by reaction with a Ziegler Natta catalyst system— this can be accomplished through either a batch or continuous process, either with or without the addition of a chain transfer catalyst.

4. The mixture of oligomers is hydrogenated and distilled to produce a $C_{12}$ and $C_{18}$ distillate, respectively.

5. Pot residue can be further vacuum distilled to produce a synthetic oil.

1. Ethanol from any source can be used in this invention. The ethanol is dehydrated to ethylene in a continuous process utilizing a low acidity alumina catalyst at elevated temperature (250-400 degrees C.) and under an inert atmosphere. Water from the dehydration process is condensed, while ethylene is thoroughly dried by passage through a suitable drying agent (i.e. molecular sieves, calcium sulfate). At this point ethylene can be condensed under increased pressure or utilized in a multi-step, downstream process. Ethanol/water solutions can also be used in the dehydration process, although higher concentrations of ethanol are another embodiment.

2. Ethylene is oligomerized to 1-hexene. When unselective catalysts are used, a fractional distillation is required to isolate pure 1-hexene. In contrast, highly selective chromium and titanium based catalysts can be utilized to produce almost exclusively 1-hexene. This can be conducted by either a batch or continuous process. The presence of heavier oligomers including 1-octene or 1-decene do not negatively impact the overall process. In another embodiment of the invention, an unselective catalyst can be used and separated into a $C_6$-$C_8$ fraction, a $C_{10}$-$C_{14}$ fraction, a $C_{16}$-$C_{20}$+fraction. The $C_6$-$C_8$ fraction can be selectively oligomerized as described below while the $C_{10}$-$C_{14}$ fraction can be directly hydrogenated and incorporated into the jet/diesel fuel formulation. The $C_{16}$-$C_{20}$ fraction can be incorporated in limited amounts in jet fuels or significant amounts in diesel fuel.

3. Pure 1-hexene, or a mixture of 1-hexene/1-octene is oligomerized to produce a product mixture primarily consisting of dimers and trimers. In the case of pure 1-hexene, the products would be 5-methyleneundecane and 7-butyl-5-methyleneundecane. Metallocene based catalysts of the group 4 elements, including Ti, Zr, Hf and other catalysts known in the art to selectively generate 1,2-addition products are suitable for this step. A cocatalyst comprised of an aluminum alkyl or methylaluminoxane is required for catalysis to take place. The cocatalyst can be added to achieve M:Al ratios of from about 1 up to about 500. The Ziegler Natta catalysts can be added in olefin: M ratios of from about 1,000,000:1 to about 5000:1. Higher catalyst loadings result in shorter reaction times. In an embodiment of the invention, a chain transfer agent such as a zinc alkyl compound can be added to alter the distribution of oligomers. The typical zinc alkyl loading for an olefin: M ratio of 100:1 is between 2 and 8 equivalents.

4. The product oligomers are catalytically hydrogenated utilizing nickel, copper, palladium, platinum, or ruthenium catalysts under a hydrogen atmosphere. Temperatures ranging from ambient up to 200 degrees C. and at pressures from 1 atm up to ~50 atm are suitable for this process. After hydrogenation, the product mixture is fractionally distilled to isolate 5-methylundecane and 7-butyl-5-methyltridecane, respectively.

5. The pot residue from the process described in 4 can be vacuum distilled at temperatures up to about 250 degrees C. to capture heavier oligomers with utility as oils and lubricants.

Despite extensive worldwide efforts to generate renewable fuels from biomass, several prominent studies have concluded that conversion of biomass to electricity is the most efficient use of these resources. Through this approach, one would envision fleets of electric vehicles powered by bio-electricity with a transition to solar electricity as capacity, photovoltaic efficiency, and storage capabilities improve. Although the widespread development of bio-electricity is important and expected to play a role in both transportation and other power requirements, it does not address the long term need for renewable jet and diesel fuels to power aircraft, heavy trucks, and ships.

Although new methods for the production of renewable fuels continue to be developed, none of these fuels have challenged the supremacy of ethanol as the dominant biofuel platform. 22 billion gallons of ethanol were produced in 2011 and this trend is expected to continue with global production of ethanol estimated at 73 billion gallons by 2030. There are a number of reasons for this remarkable projected output. First, the technology required to generate ethanol at impressive titers and with robust microorganisms has been around for thousands of years. Second, the infrastructure required to produce ethanol on a massive scale is already in place along with well-established methods for the purification, distribution, and formulation of ethanol with petroleum-based fuels. Third, a considerable amount of effort has been expended to efficiently generate ethanol from cellulosic feedstocks. This emerging technology has the potential to deliver significant quantities of fuel in a sustainable manner and according to a recent DOE study, conversion of waste biomass to renewable fuels can sustainably offset up to 30% of U.S. transportation fuels. To take advantage of the increasing production of bio-ethanol, new approaches for converting it to full-performance jet and diesel fuels need to be developed.

The first step in generating a full-performance (drop-in) renewable fuel is to remove oxygen. In the case of ethanol, this can be readily accomplished by dehydration to ethylene. This process can be conducted with widely available industrial catalysts including y-alumina, zeolites, and heteropolyacids. Some of the most promising catalysts based on phosphorus/lanthanum modified HZSM-5 give 100% conversion of ethanol with greater than 99% selectivity to ethylene. Compared to other biofuel deoxygenation methods, the generation of a gaseous hydrocarbon greatly simplifies the purification process, while the product can be stored under pressure or transferred via a pipeline. Some dehydration catalysts can be used in the presence of significant quantities of water which allows for ethanol concentration and conversion steps to be combined. Dual purpose catalysts have been developed that both dehydrate ethanol and oligomerize the resulting ethylene to generate gasoline-range hydrocarbon mixtures and even higher molecular weight distillate fuels. Although this combined approach offers a number of advantages including simplified reactor constructs without the need for additional heating/cooling cycles, the product distribution is difficult to control and a significant amount of light hydrocarbons are generated.

In addition to ethylene derived from bio-ethanol, increasing amounts are now being produced in the United States from abundant shale gas. Regardless of the source, synthetic fuels based on ethylene will be well poised to take advantage of this important resource and may offer efficient alternatives to conventional gas-to-liquids (GTL) fuel production processes.

The most straightforward route for conversion of ethylene to jet and diesel fuels relies on direct oligomerization of ethylene. This process, conducted with the aid of heterogeneous catalysts, has been well studied. One of the earliest olefin oligomerization catalysts supported polyphosphoric acid. More recently, studies have focused on ethylene oligomerization with zeolites and acidic mesoporous catalysts. For all of these catalysts the conversion to diesel range hydrocarbons is low. Acidic catalysts oligomerize olefins through carbocation intermediates. Due to the greater stability of tertiary carbocations, these catalysts generate highly branched hydrocarbons. Although these hydrocarbons are excellent for gasoline and some of the heavier branched hydrocarbons are suitable for incorporation in jet fuel, they cannot be used extensively in diesel fuel due to their low cetane numbers. A way to extend the hydrocarbon chain length to improve the cetane number is to incorporate active metals (i.e. nickel) into zeolites, and amorphous or mesoporous silica-alumina catalysts. In the latter case, yields of $C_{10+}$ oligomers have been reported in the range of 23-41% by mass. More recently, a two-step process that consisted of conversion of ethylene to a mixture of C4-C10 olefins over nickel-exchanged AlMCM-41, followed by acid-catalyzed reaction over H—MCM-41, was capable of generating jet/diesel range fuels.

To overcome the difficulties in selectively generating jet and diesel range hydrocarbons from ethanol, we became interested in utilizing 1-hexene as a renewable C6 platform for fuel synthesis (FIG. 1). There are a number of reasons why 1-hexene is intriguing as an intermediate to full-performance fuels. First, with a boiling point of 63° C., 1-hexene can be stored and transported in a similar manner to gasoline. Second, 1-hexene is an important industrial chemical used as a co-monomer with ethylene for the generation of linear low-density polyethylene and is produced on a commercial scale. Finally, 1-hexene can be efficiently generated from ethylene with the aid of a variety of homogenous catalysts.

Figure 7:
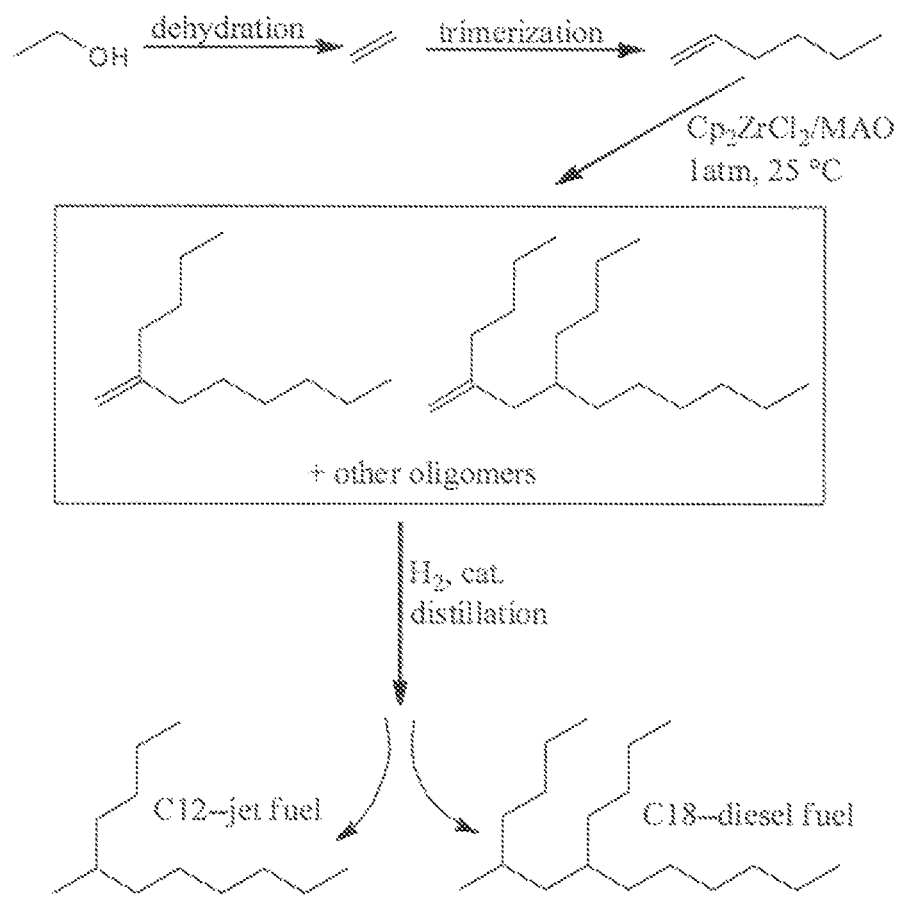
FIG. 7 is a flow chart showing conversion of ethanol to full-performance jet and diesel fuels, according to embodiments of the invention.

The most prominent examples of homogenous ethylene oligomeriation catalysts are the SHOP (Shell Higher Olefin Process)-type catalysts which generate a broad range of linear oligomers from ethylene. With regard to selective oligomerization methods, the most elegant examples can be found for ethylene trimerization. Chromium catalysts as well as titanium, zirconium, and tantalum based catalysts have been shown capable of converting ethylene to 1-hexene with selectivities up to 99% under moderate conditions. Other relevant work on the development of C6 platforms for renewable fuels has focused on biosynthetic routes to 1-hexanol, while recent reports have described the biosynthesis of caproic acid from dilute ethanol and the conversion of caproic acid to 1-hexanol with carboxydotropic bacteria. Regardless of the source, bio-1-hexanol can be converted to 1-hexene with selectivities above 95% for the normal olefin by dehydration with γ-alumina at 300° C. FIG. 7 shows a conversion of ethanol to full-performance jet and diesel fuels Given the promise of bioderived ethylene and 1-hexene as deoxygenated precursors to full-performance fuels, the current work discusses the oligomerization of 1-hexene to selectively generate both jet and diesel fuels.

Some of our previous work in the synthesis of renewable fuels and plasticizers focused on the use of bio-1-butene (ideally derived from n -butanol) as a feedstock to jet and diesel fuels. In that work, primarily trimer and tetramer (C12 and C16), were targeted so that the resulting hydrocarbon mixture would have a suitable flashpoint and density. A $Cp_2ZrCl_2$/MAO catalyst with an Al/Zr ratio of 100 was utilized to increase the amount of trimer and tetramer, while reducing the amount of dimer formed. In the case of 1-hexene, the two oligomers of interest are the dimer and trimer (C12 and C18) and this required a change in the distribution of products. A variety of zirconocene-based catalysts have been studied for hexene oligomerization, but as the commercially available $Cp_2ZrCl_2$ has been shown to possess suitable activity and the ability to produce specific product distributions, it was used in the current work. To eliminate higher molecular weight oligomers, a low Al/Zr ratio can be used, but at the expense of the TON.

To generate primarily dimer, but sufficient trimer to fully investigate its properties, the catalyst was prepared by addition of 50 equivalents of MAO to $Cp_2ZrCl_2$ followed by removal of both the solvent and residual $AlMe_3$ in vacuum. 1-hexene was used as both the solvent and the reactant and shortly after addition of 1-hexene, a clear red solution was formed. Although it was somewhat surprising that the catalyst would have sufficient solubility in the non-polar alkene to give a homogenous solution, it is likely that the catalyst only becomes soluble after coordination/insertion of the olefin. The TON of the catalyst approached 5000 and although higher TONs could be achieved, the ratio of catalyst to olefin was selected so that full conversion of 1-hexene was obtained and the reaction was complete after 16 hours at ambient temperature. Initially the reaction was exothermic and the addition had to be carefully controlled in order to keep the temperature stable. GC analysis of the product mixture showed that >80% of the product was dimer and trimer with 13% tetramer, 5% pentamer, and 1% hexamer.

Based on both the GC and NMR data, 1-hexene undergoes exclusively 1,2-addition under the reaction conditions. No stereochemical control is exerted by the catalyst which leads to the presence of diasteriomeric alkenes for oligomers with n≥4. These diasteriomers are readily observed in the GC chromatogram, although sufficient resolution was not obtained to fully separate the two tetramer isomers. The heavier oligomers are not suitable for use as fuels, but hydrogenated versions are expected to have utility as high-performance lubricants. The dimer was separated by fractional distillation at atmospheric pressure, while the trimer was separated by fractional distillation under reduced pressure to give pure samples of each hydrocarbon. Small traces of the next highest oligomer were observed by GC but not by NMR spectroscopy. The pure alkenes were then hydrogenated over Pd/C to yield the saturated compounds. This step is essential to improve the stability of the fuels. In the case of the trimer, hydrogenation yielded a pair of diasteriomers due to the presence of two stereocenters, but the similarity of the chemical shifts between the two molecules resulted in resolution of only 24 peaks in the $^{13}C$ NMR. For use as fuels, the presence of diasteriomers is important for depressing the freezing point and improving the low temperature viscosity of the hydrocarbons.

After the initial characterization of the pure saturated hydrocarbons, their key fuel properties were determined (Table 1). The density of the dimer fuel is 0.75 g/mL, below the specification for commercial jet fuel and the military jet fuel JP-8 (d>0.775 g/mL). This is common for acyclic paraffins and synthetic paraffinic kerosene (SPK) fuels that make up the bulk of renewable jet fuels. The lower density of the kerosenes compared to conventional jet fuel is due to the lack of aromatics and cycloparaffins in the renewable fuels. The trimer, with a density of 0.78 g/mL does meet the required density for jet fuel, but its relatively high viscosity would preclude its use as a standalone fuel. To address density and viscosity issues, as well as to incorporate aromatics which are essential for maintaining engine integrity, these fuels can be mixed with conventional hydrocarbon fuels. In fact, emerging renewable fuels are commonly tested as 50:50 blends with petroleum based fuels. Another key property of alternative fuels is their flashpoint. Both the dimer and trimer have significantly higher flashpoints than JP-8, and even high flashpoint jet fuel used by the US Navy (JP-5>60° C.). These high flash points greatly reduce the risk of fire and make these fuels well suited for use in demanding environments.

TABLE 1

Key Fuel Properties of Hexene Oligomer Fuels

| Property | Dimer | Trimer | Dodecane | JP-8 |
|---|---|---|---|---|
| Density (g/mL) | 0.75 | 0.78 | 0.75 | 0.80 |
| Flashpoint (° C.) | 74 | 128 | 74 | >38 |
| Viscosity (−10° C.)[a] | 3.03 | 17.2 | solid | <8.0[b] |
| Viscosity (40° C.)[a] | 1.10 | 3.1 | NM | NA |
| Cetane No. | 67 | 92 | 88 | >42 |
| Freezing Point (° C.) | −77 | — | −9 | <−47 |

[a]units: mPa·s.
[b]at −20° C.

To further evaluate these hydrocarbons as both diesel and jet fuels, the viscosities of the dimer and trimer were measured from 40 to −14° C. As expected, the dimer maintained an exceptionally low viscosity over the entire measured range. The 40° C. viscosity was only 1.10 mPa·s, with a linear increase up to 3.27 mPa·s at −14° C. The viscosity specification for diesel #2 requires a 40° C. viscosity of 2.1 mPa·s, while the −20° C. viscosity is well within the specification for JP-8 (<8.0 mPa·s), with an extrapolated value of 3.56 mPa·s. The trimer has a 40° C. viscosity of 3.1 mPa·s, which is in the middle of the range for diesel #2 (2.1-4.1 mPa·s), while the −20° C. viscosity is 24.5 mPa·s and well above the upper limit for jet fuel. Based on this data, it's clear that the dimer has properties commensurate with jet fuel, while the trimer has properties consistent with diesel fuel. Although each fuel has a direct application, it follows that significant amounts of the dimer could be blended with conventional diesel fuel and conversely, significant amounts of the trimer could be blended with petroleum-derived jet fuel.

In addition to viscosity, an acceptable freezing point is critical for jet fuels. Low temperatures at high altitude require freezing points below −47° C. for JP-8. Differential scanning calorimetry (DSC) was initially utilized to determine the freezing point of both the hydrogenated dimer and trimer, however, neither sample showed a significant endotherm during the heating cycle, nor an exotherm during the cooling cycle. Based on recent success in probing low temperature transitions of fuels with TMA, this technique was applied in the current case. The dimer exhibited a sharp transition at −77° C. corresponding to the freezing point. The glass transition temperature of this hydrocarbon could also be observed as a slow change in the probe height at −123° C. A freezing point for the trimer could not be determined, but the $T_g$ was observed at −100° C. This excellent low temperature performance can be compared to conventional diesel #2 which begins to cloud at ~0° C. and gels at ~10° C.

A key parameter for diesel fuel is the cetane number. This value is a measure of the relative ability of hydrocarbons to combust under compression ignition conditions. Hydrocarbons with long, straight chains improve the cetane number of fuel, while aromatics and branched chain hydrocarbons greatly decrease the cetane number. In the current case the hydrocarbons are modestly branched, i.e. (one branch site)/(12 carbons) for the dimer and (one branch site)/(9 carbons) for the trimer. Although methyl branches are quite prevalent in conventional fuels, butyl branches are not and it was unclear what effect the modest branching of the trimer would have on the cetane number. In our previous experience with butene oligomer fuels, it was observed that a blend of C12 and C16 molecules with 2 or 3 branches, respectively, had a cetane number of 55. Based on this result, we expected the hexene-derived fuels to have cetane numbers greater than 60. The cetane number for pure solutions of both the dimer and trimer were determined by IQT. The dimer had a cetane number of 67, while the trimer had a remarkable cetane number of 92. These values are less than the linear alkanes of the same molecular weight, with dodecane having a cetane number of 88 and n-octadecane having a cetane number of 103, but quite remarkable compared to diesel #2 which only requires a cetane number of 42. The exceptional cetane numbers of these renewable fuels suggests that they may have utility as blendstocks to improve the cetane number of petroleum-based fuels.

In summary, renewable jet and diesel fuels can be readily generated from 1-hexene by a controlled oligomerization process. Coupling the current work with the near quantitative yields reported in the literature for ethanol dehydration and ethylene trimerization, the overall process for converting bio-ethanol to jet/diesel fuels and biolubricants is >92% carbon efficient. Due to the exquisite control of the products imparted by the metallocene catalyst, the fuels produced by this method can in some cases outperform conventional petroleum-based fuels. The synthesis of renewable hydrocarbons that significantly improve the performance characteristics of petroleum based fuels represents a paradigm shift in the development of alternative fuels.

The outlook for producing these fuels on an industrial scale is promising. Given the existing infrastructure for the production and utilization of both ethylene and 1-hexene, the current process could be readily integrated into existing facilities. The versatility of this approach which can utilize either bio-ethanol or petrochemical ethylene as a feedstock renders this process a dynamic alternative to other bottom-up synthetic jet/diesel production processes including conventional GTL technology and Fischer-Tropsch catalysis.

Embodiments of the invention generally relate to methods for converting ethanol to turbine and/or diesel fuels including, dehydrating ethanol by the use of at least one heterogeneous catalyst to produce ethylene, converting the ethylene into 1-hexene by reacting the ethylene with a selective or unselective oligomerization catalyst to produce pure 1-hexene or a mixture including 1-hexene, converting the 1-hexene into a mixture of dimer(s) and trimer(s) by reacting the 1-hexene with a Ziegler Natta catalyst, and hydrogenating with a hydrogenation catalyst and distilling the mixture of dimer(s) and trimer(s) to produce a $C_{12}$ turbine/jet fuel, $C_{18}$ diesel fuel, and residues.

In embodiments, the ethanol is dehydrated to the ethylene in a continuous process utilizing a low acidity alumina catalyst at elevated temperature ranging from about 250° C. to about 400° C. and under an inert atmosphere. In embodiments, the ethylene is thoroughly dried by passage through a suitable drying agent. In other embodiments, the ethylene is condensed under increased pressure or utilized in a multi-step, downstream process. In embodiments, the unselective catalyst(s) and a fractional distillation is used to isolate pure 1-hexene. Embodiments further include separating into a $C_6$-$C_8$ fraction, a $C_{10}$-$C_{14}$ fraction, a $C_{16}$-$C_{20}$ fraction, and a $C_{20}$+ fraction when the unselective oligomerization catalyst(s) is used. In embodiments, the $C_6$-$C_8$ fraction is selectively oligomerized with a Ziegler-Natta catalyst, the $C_{10}$-$C_{14}$ fraction is directly hydrogenating and incorporating into the jet/diesel fuel formulation, and the $C_{16}$-$C_{20}$ fraction is incorporating in limited amounts up to about 20% in jet fuels or significant amounts in diesel fuel.

In embodiments, the Ziegler-Natta catalyst(s) are metallocene based catalysts of the group 4 elements selected from the group consisting of Ti, Zr, Hf, other like catalysts, and any combination thereof. Embodiments further include adding at least one cocatalyst including aluminum alkyls or methylaluminoxane. In embodiments, the 1-hexene is pure 1-hexene or a mixture of 1-hexene/1-octene and is oligomerized to produce a product mixture primarily of the dimers and trimers. In embodiments, when using the pure 1-hexene, the products are 5-methyleneundecane and/or 7-butyl-5-methyleneundecane. In embodiments, the cocatalyst(s) is added to achieve M:Al ratios of from about 1 up to about 500 and said Ziegler Natta catalyst(s) is added in olefin: M ratios of from about 10,000,000:1 to about 5000:1.

In embodiments, the ethylene is generated from a renewable source and/or a petrochemical source. In other embodiments, the ethanol is from a renewable source selected from the group consisting of sugars, cellulosic or lignocellulosic feedstocks, $CO_2$, and bio-derived syngas. In embodiments, the heterogeneous catalyst(s) includes alumina. In embodiments, the oligomerization catalyst includes an ethylene trimerization catalyst that is Ti, Cr, Ta, or Zr-based. In other embodiments, the catalyst includes a highly selective chromium and titanium based catalyst(s) utilized to produce exclusively 1-hexene. In embodiments, the second Ziegler Natta catalyst is either a batch or continuous process.

Embodiments further include adding at least one chain transfer catalyst. In other embodiments, the chain transfer agent is a zinc alkyl compound added to alter the distribution of the dimer(s) and trimer(s) (oligomers), In embodiments, the zinc alkyl loading for an olefin is M ratio of 100:1 is between 2 and 8 equivalents. Embodiments, further include catalytically hydrogenating the dimer(s) and trimer(s)(oligomers) with catalysts selected from the group consisting of nickel, palladium, platinum, and ruthenium catalysts under a hydrogen atmosphere. In embodiments, the hydrogenation includes temperatures ranging from ambient up to 200° C. and at pressures from 1 atm up to about 50 atm. In embodiments, the residue is further vacuum distilled to produce synthetic oil. Another aspect of the invention relates to turbine and diesel Fuels produced by the methods described herein.

Fuels derived from bisabolene can have volumetric net heats of combustion comparable to JP-10 and can be produced from biomass sugars.

The range of aircraft and weapon systems is largely dependent on the fuel used for propulsion. Fuels based on the monocyclic structure of bisabolane have volumetric net heats of combustion higher than conventional Navy jet fuel (JP-5) while maintaining an acceptable cetane number (>40). Further, bisabolene has three alkene groups which can be catalytically isomerized to generate fuels with net heats of combustion higher than JP-10 (>141,500 btu/gal). In addition, bisabolene can be generated from sustainable biomass sugars via fermentation. Use of these fuels will reduce net carbon emissions while improving the range and loiter time of a variety of Navy platforms.

1. alpha-bisabolene is generated via a fermentation process from substrates including biomass sugars and natural gas. Alternatively, alpha-bisabolene can be isolated from a renewable source, or generated by a metabolically engineered plant.

2. Bisabolene is catalytically isomerized to multicyclic hydrocarbons or bisabolene is dimerized to C30 hydrocarbons.

3. The product mixture is hydrogenated to yield a saturated mixture.

4. If desired the saturated mixture including cedranes can be further isomerized to diamondoid structures.

5. Hydrogenated mixtures can be used directly as fuels or blended with other fuels to achieve desired properties.

Additives, including cetane enhancers can be added to the reduced sesquiterpenes to generate full performance jet or diesel fuels.

The following is a detailed description of some embodiments of the invention.

1. Alpha-bisabolene is generated from substrates including biomass sugars or natural gas via a fermentation process. Feedstocks can include cellulose, hemicellulose, glucose, sucrose, other reducing sugars, cellobiose, crude lignocellulosic materials, and lignin. Alternatively, mixtures of sesquiterpenes including bisabolenes can be isolated from plant extracts by steam distillation.

2. Bisabolenes are catalytically isomerized to multicyclic hydrocarbons with acid catalysts.

In embodiments the product mixture obtained via isomerization includes cedrenes. In embodiments the product mixture includes a complex mixture of multicyclic hydrocarbons.

In embodiments the reaction can be allowed to go to completion or stopped at lower degrees of conversion to generate mixtures of bisabolenes and multicyclic sesquiterpenes. In embodiments the catalysts are heterogeneous acid catalysts. In embodiments, the bisabolene undergoes dimerization to yield multicyclic C30 hydrocarbons. In other embodiments, a mixture of multicyclic sesquiterpenes and C30 hydrocarbons are generated. The multicyclic hydrocarbons can then be separated by fractional distillation.

3. Antioxidants including phenolics are added to the unsaturated sesquiterpene mixture to increase the storage stability of the hydrocarbons. In a preferred embodiment, the sesquiterpene mixture is hydrogenated in the presence of a catalyst under a hydrogen atmosphere to obtain a saturated sesquiterpene mixture. A fuel mixture including only unsaturated bisabolene has the following properties: a net heat of combustion of 134, 150 btu/gal, a −20° C. viscosity of 10.5 cP, a 40° C. dynamic viscosity of 1.92 cP, and a density of 0.87 g/mL. A fuel mixture including only bisabolane has a net heat of combustion of 127,500 btu/gal, a −20° C. dynamic viscosity of 17.2 cP, a 40° C. dynamic viscosity of 2.1 eP, and a density of 0.814 g/mL. A fuel composed of hydrogenated cedrene has a net heat of combustion of ca. 142,000 btu/gal and a density of ca. 0.92 g/mL. Mixtures of bisabolane and cedrane have densities between 0.81 and 0.92 g/mL and NHOCs from 127-142,000 btu/gal. In embodiments saturated C15 hydrocarbons are separated from C30 dimers by fractional distillation after hydrogenation. The C30 hydrocarbons have applications as synthetic lubricants.

4. C15 mixtures including cedrenes or cedranes can be isomerized with a Lewis acid catalyst to yield hydrocarbons with diamondoid structures. In embodiments the diamondoid is 1-ethyl-3,5,7-trimethyladarnantane.

5. Fuel mixtures including unsaturated sesquiterpene blends, saturated sesquiterpene blends, or diamondoid blends are combined with other renewable or petroleum-based fuels. In embodiments the sesquiterpene-derived fuels are blended with Jet-A, JP-8, JP-5, JP-10, RJ-4, F-76, commercial diesel fuel. In other embodiments, the sesquiterpene/pane fuels are blended with high cetane fuels derived via a Fischer-Tropsch process or Alcohol to-Jet (ATJ) process to generate fuels with cetane numbers in the range of 30-50. In other embodiments the sesquiterpene fuels are blended with nitrate esters or other cetane enhancers in low concentration to yield fuels with increased cetane numbers. In embodiments, further includes bisabolane blended with multicyclic sesquiterpanes or diamondoids to lower the viscosity of derivative fuels. In other embodiments, further includes bisabolane blended with multicyclic sesquiterpanes to improve the cetane number of the fuel in the range of 30-45.

Embodiments of the invention generally relate to methods for manufacturing jet and diesel fuels including, providing at least one α-bisabolene A, a mixture of bisabolenes B, or a mixture of sesquiterpenes C including bisabolenes generated by metabolically engineered organisms from substrates including glucose, sucrose, fructose, other reducing sugars, cellobiose, cellulose, hemicellulose, lignocellulose, and methane, or isolated from plant material by solvent extraction or steam distillation, isomerizing the α-bisabolene or bisabolene mixtures with a heterogeneous or homogenous acid catalyst to produce isomers, hydrogenating the isomers with at least one hydrogenation catalyst under hydrogen pressure and distilling the isomers to produce a first high density fuel and a higher molecular weight residue, or further isomerizing the isomers with a Lewis acid catalyst to generate a hydrocarbon mixture including adamantanes and distilling the adamantane mixture to produce a second high density fuel mixture and a higher molecular weight residue.

In embodiments, the isomer mixture includes multicyclic sesquiterpenes. In other embodiments, the isomer mixture includes cedrenes. In embodiments, the residue obtained after distillation of the first high density fuel is purified by vacuum distillation to yield a lubricant composed primarily of C30 hydrocarbons. In embodiments, the second high density fuel mixture having 1-ethyl-3,5,7-trimethyladamantane and other alkyladamantanes. In embodiments, the hydrogenating catalyst has at least one metal selected from the group consisting of Ni, Cu, Pd, Pt, Ru. In embodiments, the first acid catalyst is selected from the group consisting of at least one of perfluorinated sulfonic acid resins, cross-linked sulfonic acid resins, acid clays, zeolites, polyphosphoric acid, cation exchange resins, Lewis acid catalysts, metal oxides, supported Brnsted acid catalysts, mineral acids including $H_2SO_4$ and $H_3PO_4$, and any mixtures thereof. In other embodiments, the Lewis acid catalyst is selected from $AlCl_3$, $AlBr_3$, $AlI_3$, Lewis acidic ionic liquids, $BF_3$, gallium triflate, indium triflate, and other strong Lewis acids.

In embodiments, the first high density fuel has a density between 0.81 and 0.92 g/mL and a volumetric net heat of combustion from 124-142,000 btu/gal. In embodiments, the second high density fuel mixture has a density between about 0.88 and 0.94 g/mL and a volumetric net heat of combustion from 135-145,000 btu/gal. In embodiments, the first high density fuel or second high density fuel mixture has a cetane number between 30 and 42. In embodiments, the first high density fuel or second high density fuel mixture has a viscosity between about 10 and 60 cP at −20° C. In embodiments, the first high density fuel or second high density fuel mixture is blended with cetane enhancers including alkyl nitrates to generate fuels with cetane numbers >40.

In embodiments, the first high density fuel or second high density fuel mixture is blended with petroleum-based fuels including JP-10, RJ-4, JP-8, JP-5, F-76, Diesel #2, and Jet A. In embodiments, the first high density fuel or second high density fuel mixture is blended with a high cetane blendstock including fuels generated via a Fischer-Tropsch process, ethylene oligomerization, butene oligomerization, hexene oligomerization, to generate fuels with cetane numbers >40. In embodiments, the lubricant has a viscosity >20 cP at 40° C. In embodiments, the purified sesquiterpenes are combined with antioxidants including BHT and/or renewable phenols, and used as fuels without hydrogenation. Embodiments further include isomerizing the pure α-bisabolene or bisabolene mixtures with at least one solvent. Another aspect of the invention generally relates to fuels produced by the methods herein.

Figure 2:
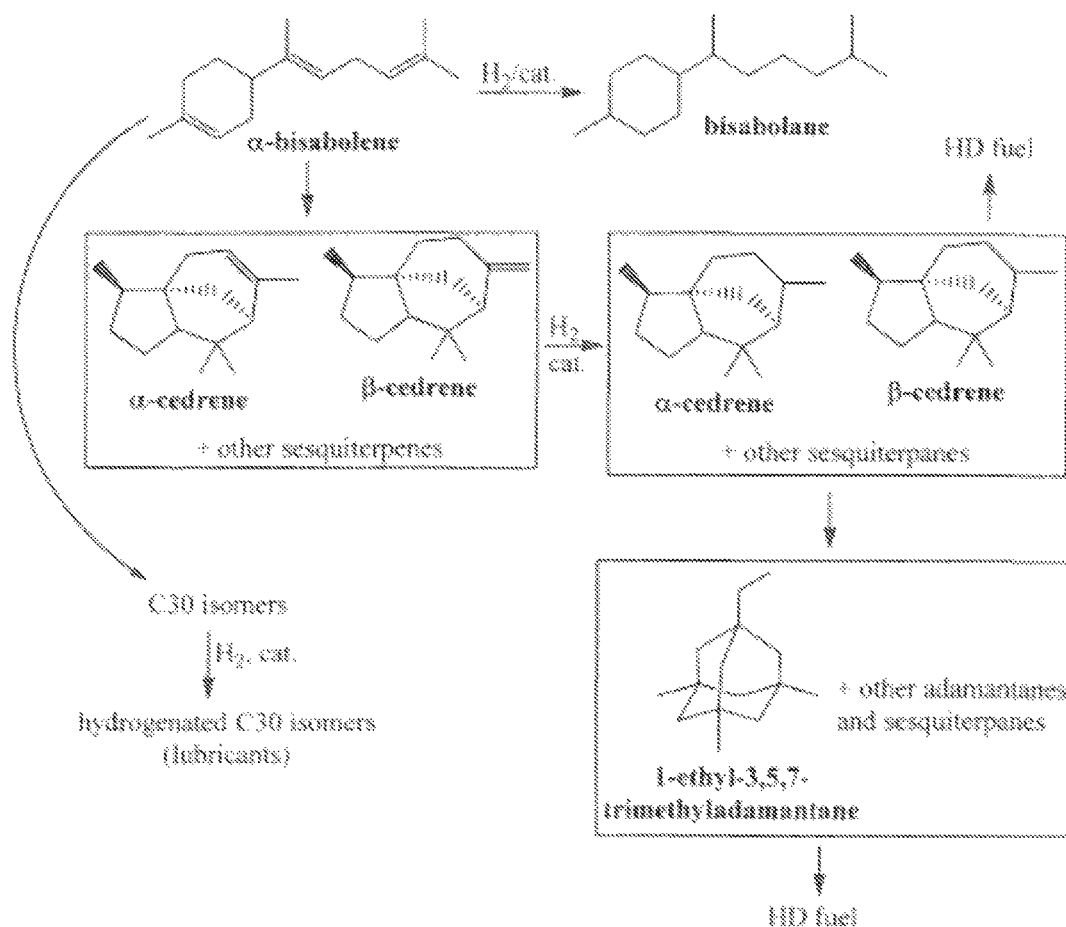
FIG. 2 is a flow diagram illustrating the synthesis of high density fuels and lubricants from α-bisabolene, according to embodiments of the invention.

FIG. 2. The catalytic conversion of α-bisabolene to high density fuels and lubricants. The experimental dynamic viscosity of α-bisabolene and bisabolane between −20 and 40° C.

The biosynthesis of farnesene and use as a standalone diesel/jet fuel or component of same is covered in the following USPTO applications: 20090272352, 20090272119, 20090020090, 20090020089, and 20080092829. Farnesane, the reduced form of farnesene, is a linear sesquiterpene of relatively low density (0.766 g/mL). U.S. Pat. No. 7,846,222 describes farnesane-based jet and diesel fuels. U.S. patent application Ser. No. 20130298861 describes biosynthetic methods to generate bisabolene and discusses some fuels derived from bisabolene.

High density fuels have applications in a variety of Navy platforms including jet aircraft, ships, missiles, and UAVs. The fuels developed herein will help to meet Navy goals focused on the use of renewable and sustainable fuels while providing improved performance over conventional, petroleum-based fuels.

Embodiments of this invention describe the conversion of sesquiterpenes to high density fuels. The sesquiterpenes can be either extracted from plants or specifically produced by bioengineered organisms from waste biomass. This approach allows for the synthesis of high performance renewable fuels.

Embodiments of the invention detail processes for conversion of sesquiterpenes to high density fuel mixtures. Aspects of the process include hydrogenation of the sesquiterpenes to improve stability of the fuels as well as selective isomerization of the sesquiterpenes to improve density, net heat of combustion, low temperature viscosity, and cetane number. The isomerization process can be carried out with heterogeneous catalysts at moderate temperatures and requires no solvent. Thus, embodiments of the invention provide a route for the sustainable production of renewable, ultra-performance fuels.

The general procedure for synthesizing high density sesquiterpene fuels is as follows:

1. A pure sesquiterpene or mixture of sesquiterpenes are either extracted from plant sources (e.g. clove oil) or 2. a) A biomass source (including lignocellulosic, cellulosic, or hemicellulosic feedstocks) is hydrolyzed to produce a sugar solution b) The sugar solution is fermented to a sesquiterpene or mixture of sesquiterpenes by a bioengineered organism.

3. The hydrocarbons are purified by solvent extraction, pervaporation, membrane separation, or distillation.

4. Pure sesquiterpenes or mixtures are then:

a) Directly hydrogenated and distilled to yield a liquid fuel or b) Isomerized with heterogeneous acidic catalysts to produce a pure compound or complex mixture of hydrocarbons which is then hydrogenated and distilled to yield a liquid fuel.

Process:

1. A pure sesquiterpene or mixture of sesquiterpenes is isolated from a plant source. This can be accomplished by steam distillation, solvent extraction, or pyrolysis, among other techniques.

2a. In an alternate approach, biomass can be hydrolyzed to produce a sugar solution. This step can be accomplished by physical, chemical, or enzymatic methods, or any combination thereof.

2b. The sugar solution is used as a food source for bioengineered organisms that produce sesquiterpenes in either a batch or continuous mode.

3. Regardless of the source, the sesquiterpenes can be upgraded through techniques including fractional distillation, chemical treatments, and extractions to produce a suitably pure hydrocarbon feedstock composed of either a single sesquiterpene or complex mixture of sesquiterpenes. In the case of the biosynthesized sesquiterpenes (2b), the major impurity is water which can be effectively removed by both membrane separation techniques as well as by distillation.

4a) Sesquiterpenes are directly hydrogenated to produce a high density fuel. Catalysts based on Ni, Pd, Pt, Cu, and Ru can be utilized under moderate hydrogen pressures.

4b) To improve specific fuel properties such as viscosity, net heat of combustion, density, and cetane number, sesquiterpenes can be readily isomerized with heterogeneous acid catalysts including, but not limited to; Nafion, Amberlyst, Montmorillonite K-10, zeolites and supported polyphosphoric acid. Sesquiterpenes can also be effectively isomerized with Lewis acids and mineral acids. After isomerization, these sesquiterpenes can be hydrogenated as in 4a. Pure sesquiterpenes or defined mixtures of sesquiterpenes can be isolated by fractional distillation to generate fuels with specific properties.

Example 1 High Catalyst Loading 50 mL of caryophyllene (technical grade) is combined with 500 mg Nafion SAC-13 in a flask. The mixture is vigorously stirred and heated to 100° C. overnight. The pale yellow solution is decanted, hydrogenated at 50 psig H$_2$ with 50 mg PtO$_2$ as catalyst. The resulting mixture is filtered and vacuum distilled to yield a colorless fuel mixture including saturated hydrocarbons derived from seven main isomers including u-neoclovene, clovene, and u-panasinsene (see Schematic 1).

Schematic 1. Products resulting from the acid-catalyzed isomerization of β-caryophyllene. Numbers under the structures represent the weight percentage of each molecule. The first number results from low catalyst loading, while the number in parantheses results from high catalyst loading as described in the process.

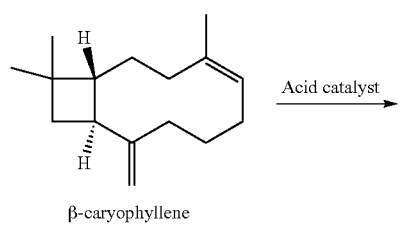

β-caryophyllene

Acid catalyst

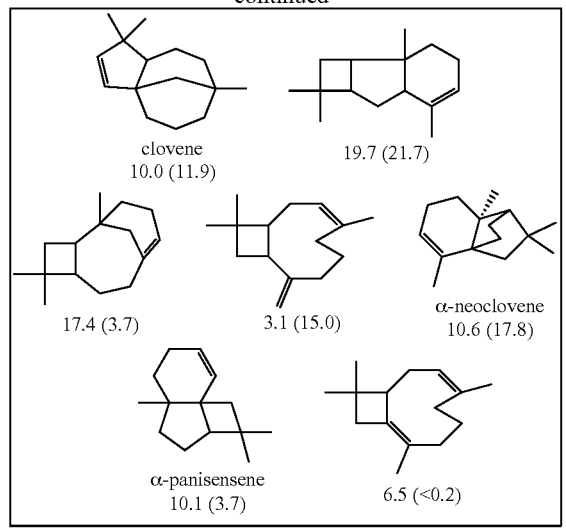

clovene
10.0 (11.9)

19.7 (21.7)

17.4 (3.7)

3.1 (15.0)

α-neoclovene
10.6 (17.8)

α-panisensene
10.1 (3.7)

6.5 (<0.2)

Example 2 (Low Catalyst Loading)

500 mL of caryophyllene is combined with 2 g of Nafion SAC-13 in a flask and subjected to the same conditions as in Example 1. A significantly different product distribution results (see Schematic 5).

Example 3

175 mL of valencene (Scheme 1) biosynthesized from sucrose is hydrogenated at 50 psig H$_2$ with 100 mg PtO2 as catalyst. After hydrogenation the catalyst flocculates and the catalyst is separated by decantation. The properties of this fuel mixture are listed in Table 2.

Example 4

175 mL of premnaspirodiene (Scheme 1) biosynthesized from sucrose is hydrogenated as in Example 3. The properties are listed in Table 2.

Example 5

175 mL of commercial caryophyllene (technical grade) is hydrogenated as in Example 3. The properties are listed in Table 2.

Example 6

5 g of valencene biosynthesized from sucrose are combined with 0.1 g of Nafion SAC-13 and the mixture is stirred and heated to 100° C. for 16 h. The solution is decanted to yield a mixture of isomers.

Example 7 5 g of premnaspirodiene biosynthesized from sucrose is isomerized as described in Example 6.

Table 2. Key Properties of Sesquiterpene Fuels.

TABLE 2

Key Properties of Sesquiterpene Fuels

| Sesquiterpene | Density (g/mL) | NHOC (btu/gal) | 40° C. Viscosity (cSt) | −20° C. Viscosity (cSt) | Ignition Delay (ms) | Derived Cetane No. |
|---|---|---|---|---|---|---|
| Valencane | 0.879 | 135,386 | 4.417 | 50.24 | 10.562 | 23.26 |
| Caryophyllane | 0.85 | 132,790 | 4.067 | 60.47 | 9.75 | 24.52 |
| Premnaspirodiane | 0.882 | 135,564 | 3.812 | 42.91 | 7.779 | 28.65 |
| HDCL-8 | 0.90 | 137,800 | 53.58 | NM | 13.173 | 20.23 |
| HDCL-9 | 0.90 | 137,100 | 5.07 | 61.96 | 6.549 | 32.53 |
| HDCL-10 | 0.92 | 140,900 | NM | NM | NM | NM |

Note: HDCL-8 is the fuel generated from caryophyllene with high catalyst loading, HDCL-9 is the fuel generated with low catalyst loading. The density and net heat of combustion of HDCL-10 has been calculated based on a distillate cut including primarily high-density components (i.e. clovene/neoclovene and assuming a density of 0.92 g/mL).

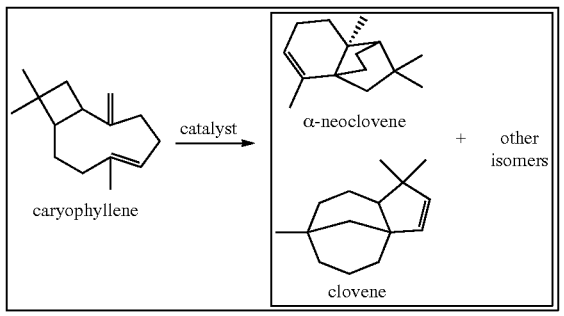

Scheme 1. Isomerization of Caryophyllene with a Heterogeneous Acid Catalyst

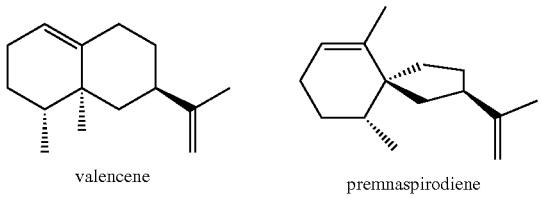

Scheme 1. Structures of valencene and premnaspirodiene.

Embodiments of the invention generally relate to methods for manufacturing jet and diesel fuels including, providing pure and/or mixed sesquiterpenes isolated from plant extracts and/or biosynthesized from biomass, purifying the pure and/or mixed sesquiterpenes to produce single components or mixtures of sesquiterpenes, converting the single component or mixed sesquiterpenes by either, directly hydrogenating the single component or mixed sesquiterpenes with at least one hydrogenation catalyst under hydrogen pressure, or isomerizing either with or without a solvent, the single component or mixed sesquiterpenes with at least one heterogeneous acid catalyst to produce isomers and hydrogenating the isomers with at least one hydrogenation catalyst under hydrogen pressure, and distilling either the hydrogenated single component or mixed sesquiterpenes or the hydrogenated isomers to produce high density fuels.

Another aspect of the invention generally relates to the production and blends of fuels. In embodiments, the pure and/or mixed sesquiterpenes are selected from the group consisting of valencene, premnaspirodiene, caryophyllene, humulene, clovene, neoelovene, panasinsene, thujopsene, longifolene, cubebene, zizaene, santalene, longipinene, isomers of the above sesquiterpenes, other cyclic terpenes, and any mixtures thereof. In embodiments, the single component or mixed sesquiterpenes are selected from the group consisting of caryophyllene, valencene, premnaspirodiene, or any mixture thereof. In embodiments, the isomers are at least one isomer selected from the group consisting of α-neoclovene, clovene, or any mixture thereof. In embodiments, the hydrogenating catalyst having at least one metal selected from the group consisting of Ni, Cu, Pd, Pt, $PtO_2$, Ru and the reaction is conducted without a solvent.

In embodiments, the heterogeneous acid catalyst are selected from the group consisting of at least one of Nafion (perfluorinated sulfonic acid resins), Amberlyst (cross-linked sulfonic acid resins), Montmorillonite K-10, zeolites, polyphosphoric acids, cation exchange resins, Lewis acid catalysts, supported Brnsted acid catalysts, mineral acids including $H_2SO_4$ and $H_3PO_4$, and any mixtures thereof. In embodiments, the plant extracts are selected from the group consisting of clove oil or any essential oil having significant quantities of cyclic sesquiterpenes, and mixtures of said oils. In embodiments, the biomass includes at least one of sucrose, glucose, fructose, cellobiose, other reducing sugars, cellulose, and hemicelluloses in any proportion.

Another aspect of the invention generally relate to methods for manufacturing jet and diesel fuels including, providing pure and/or mixed sesquiterpenes isolated from plant extracts and/or biosynthesized from biomass, purifying the pure and/or mixed sesquiterpenes to produce single components or mixtures of sesquiterpenes producing a first set of fuels, or converting the single component or mixed sesquiterpenes by isomerizing either with or without a solvent, the single component or mixed sesquiterpenes with at least one heterogeneous acid catalyst to produce isomers, and distilling the isomers producing a second set of fuels. All blends of fuels are incorporated into all aspects of the invention.

Yet other aspects of the invention generally relate to a first set of fuels produced from the methods above. Still yet other aspects of the invention generally relate to a second set of fuels produced from the methods above.

In embodiments, the fuels are pure sesquiterpanes or prepared by selective fractional distillation of sesquiterpane mixtures (density>0.90 g/mL, NHOC>137,000 btu/gal). In other embodiments, the fuels are pure sesquiterpanes or generated by selective fractional distillation of sesquiterpane mixtures (cetane number>30). In yet other embodiments, the fuels are generated by blending sesquiterpane mixtures with known cetane enhancers or antioxidants for fuels. In embodiments, the fuels generated by blending sesquiterpene fuels with petroleum-based fuels including JP-10, RJ-4, JP-8, JP-5, F-76, Diesel #2, Jet A, and any renewable fuel.

In embodiments, the high density missile/turbine fuels are blends of cyclic sesquiterpanes with JP-10 in a desired proportion. In embodiments, the high density jet fuels are blends of cyclic sesquiterpanes with jet fuels including JP-5, JP-8, and Jet A. In embodiments, the high density diesel fuels are blends of cyclic sesquiterpanes with petroleum-derived diesel fuel. In embodiments, the high density jet/diesel fuels are blends of cyclic sesquiterpanes with fuels generated by ethylene oligomerization. In embodiments, the high density jet/diesel fuels are blends of cyclic sesquiterpanes with fuels generated by butene oligomerization. In embodiments, the high density jet/diesel fuels are blends of cyclic sesquiterpanes with fuels generated by hexene oligomerization. In embodiments, the high density jet/diesel fuels are blends of cyclic sesquiterpanes with diesel fuels produced from natural gas.

Fuels based on barbatene and thujopsene have volumetric energy densities comparable to JP-10 and can be produced from biomass sugars and other renewable substrates. The range of aircraft and weapon systems is largely dependent on the fuel used for propulsion. Fuels based on the multicyclic structures of barbatene and thujopsene have volumetric net heats of combustion up to 15% higher than conventional Navy jet fuel (JP-5). Moreover, blends of barbatene, thujopsene, and other sesquiterpenes can be generated from sustainable feedstocks via fermentation. Use of these fuels will reduce net carbon emissions while improving the range and loiter time of a variety of Navy platforms.

1. Barbatene/thujopsene mixtures are generated via a fermentation process from biomass sugars or natural gas. Alternatively these sesquiterpene mixtures can be isolated from a renewable source, or generated by a metabolically engineered plant.

2. The sesquiterpene blend is purified by fractional distillation or used as a mixture of sesquiterpenes.

3. Alternatively, the mixture can be dimerized to yield a mixture rich in C30 hydrocarbons.

4. The product mixture is hydrogenated to yield a saturated mixture.

5. Saturated mixtures are suitable as standalone fuels or blended with other fuels to achieve desired properties. Additives, including octane enhancers can be added to the reduced sesquiterpenes to generate full-performance jet or diesel fuels. Dimerized mixtures have utility as lubricants.

The following are some embodiments of the invention.

1. A mixture of barbatene, thujopsene, acoradiene, beta-chamigrene and alpha-cuparene along with other sesquiterpenes is generated from substrates including biomass sugars or natural gas via a fermentation process. Feedstocks can include cellulose, hemicellulose, and lignocellulosic materials. Alternatively, mixtures of sesquiterpenes including barbatene and thujopsene can be isolated from plant extracts by steam distillation.

2. In embodiments, a mixture comprising about 15% thujopsene, 30% alpha-barbatene, 10% beta-chamigrene, 10% beta acoradiene, 5% cuparene along with additional sesquiterpenes is isolated. In other embodiments, a thujopsene/barbatene enriched mixture is isolated by fractional distillation.

3. In embodiments the thujopsene/barbatene mixture is dimerized to generate a lubricant mixture. thujopsene/barbatene can be dimerized thermally or in the presence of a homogenous or heterogeneous catalyst. In embodiments the catalyst is an acid catalyst including zeolites, aluminosilicates, clays, cation exchange resins, etc.

4. Antioxidants including phenolics are added to the unsaturated sesquiterpene mixture to increase the storage stability of the hydrocarbons. In a preferred embodiment, the sesquiterpene mixture is hydrogenated in the presence of a catalyst under a hydrogen atmosphere to obtain a saturated sesquiterpene mixture. In embodiments, a catalyst selective for the hydrogenation of alkenes, but unreactive with cyclopropane rings is used for the hydrogenation. Through this method, the skeletal structure of thujopsene remains intact and allows for a higher volumetric and gravimetric net heat of combustion. In embodiments the hydrogenation is conducted in acetic acid. In embodiments, the unsaturated fuel has a density of 0.93 g/mL, a volumetric net heat of combustion (NHOC) of 144 kBtu/gal, a flashpoint of 98° C., a −20° C. dynamic viscosity of 34.9 cP, a 40° C. dynamic viscosity of 3.93 cP, and a glass transition temperature of −91° C. In embodiments, the saturated sesquiterpene mixture has a density of 0.901 g/mL, a volumetric net heat of combustion of 138-140 kBtu/gal, a −20° C. dynamic viscosity of 46.9 cP, a 40° C. dynamic viscosity of 4.9 cP, and a glass transition temperature of −97° C. In other embodiments, either the unsaturated or saturated sesquiterpene mixture is isomerized with an acid catalyst for the purposes of decreasing the viscosity, increasing the density and net heat of combustion, or increasing the cetane number. In embodiments, the product of the isomerization reaction includes a diamondoid structure. In embodiments the isomerized mixture is purified by fractional distillation.

5. Fuel mixtures including unsaturated sesquiterpene blends and saturated sesquiterpene blends are combined with other renewable or petroleum-based fuels. In embodiments the sesquiterpene fuels are blended with Jet-A, JP-8, JP-5, JP-10, RJ-4, F-76, commercial diesel fuel. In other embodiments, the sesquiterpene/pane fuels are blended with high cetane fuels derived via a Fischer-Tropsch process or Alcohol-to-Jet (ATJ) process to generate fuels with cetane numbers in the range of 30-50. In other embodiments the sesquiterpene/pane fuels are blended with nitrate esters or other cetane enhancers in low concentration to yield fuels with increased cetane numbers.

Embodiments of the invention generally relate to methods for manufacturing turbine and diesel fuels including, providing a sesquiterpene mixture having barbatene and thujopsene, and generated by metabolically engineered organisms from substrates including glucose, sucrose, fructose, other reducing sugars, cellobiose, cellulose, hemicellulose, lignocellulose, lignin, methane, and $CO_2$, or isolated from plant material by solvent extraction or steam distillation, purifying the sesquiterpene mixture to produce pure barbatene or pure thujopsene or pure sesquiterpene mixtures, isomerizing the pure barbatene, thujopsene, or sesquiterpene mixtures with at least one heterogeneous or homogenous acid catalyst to produce isomers, hydrogenating the isomers with at least one hydrogenation catalyst under hydrogen pressure, and distilling the isomers to produce a first high density fuel and a higher molecular weight residue, or further isomerizing the isomers with at least one Lewis acid catalyst to generate a hydrocarbon mixture including adamantanes and distilling the adamantine mixture to produce a second high density fuel mixture and a higher molecular weight residue.

In embodiments, the sesquiterpene mixture having >12 weight % thujopsene and >25 weight % barbatene. In embodiments, the sesquiterpene mixture has thujopsene, alpha-barbatene barbatene, beta-chamigrene, beta-acoradiene, and cuparene in any proportional combination thereof. In embodiments, the residue obtained after distillation of the first or the second high density fuel is purified by vacuum distillation to yield a lubricant composed primarily of C30 hydrocarbons. In embodiments, the hydrogenating catalyst has at least one metal selected from the group consisting of Ni, Cu, Pd, Pt, and Ru. In embodiments, the heterogeneous or homogenous acid catalyst is selected from the group consisting of at least one of perfluorinated sulfonic acid resins, cross-linked sulfonic acid resins, acid clays, zeolites, polyphosphoric acid, cation exchange resins, Lewis acid catalysts, supported Brnsted acid catalysts, mineral acids including $H_2SO_4$ and $H_3PO_4$, and any mixtures thereof. In embodiments, the Lewis acid catalyst is selected from $AlCl_3$, $AlBr_3$, $AlI_3$, Lewis acidic ionic liquids, $BF_3$, gallium triflate, indium triflate, and other strong Lewis acids, and any combinations thereof.

In embodiments, the first or second high density fuel has a density between 0.88 and 0.93 g/mL and a volumetric net heat of combustion >138,000 btu/gal. In embodiments, the high density fuel or the second high density fuel mixture is blended with cetane enhancers including alkyl nitrates to generate fuels with cetane numbers >40. In embodiments, the first high density fuel or the second high density fuel mixture has a dynamic viscosity between about 30 and 50 cP at −20° C. In embodiments, the first high density fuel or the second high density fuel mixture has a dynamic viscosity <5 cP at 40° C. In embodiments, the first high density fuel or the second high density fuel mixture is blended with petroleum-based fuels including JP-10, RJ-4, JP-8, JP-5, F-76, Diesel #2, and Jet A.

In embodiments, the first high density fuel or the second high density fuel mixture is blended with a high cetane blendstock including fuels generated via a Fischer-Tropsch process, ethylene oligomerization, butene oligomerization, or hexene oligomerization, to generate fuels with cetane numbers >40. In embodiments, the lubricant has a dynamic viscosity >20 cP at 40° C. In embodiments, the purified sesquiterpenes are combined with antioxidants including BHT, and/or renewable phenols, and used as fuels without hydrogenation. Another aspect of the invention generally relates to methods for manufacturing turbine and diesel fuels including, providing a sesquiterpene mixture having barbatene and thujopsene, and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation, purifying the sesquiterpene mixture to produce pure barbatene or thujopsene or sesquiterpene mixtures, hydrogenating the pure barbatene or thujopsene or sesquiterpene mixture with at least one hydrogenation catalyst under hydrogen pressure; and distilling the isomers to produce a high density fuel.

Figure 3:
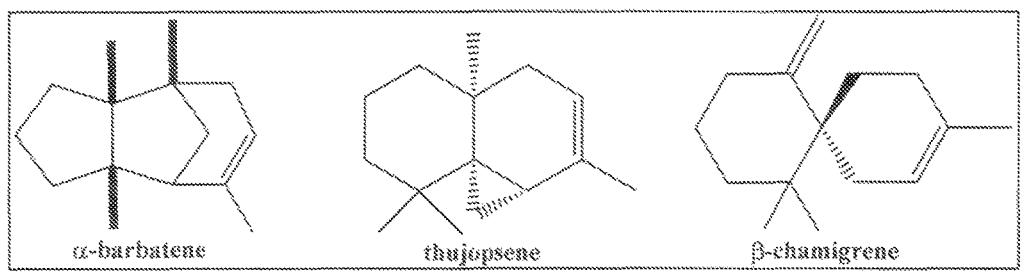
FIG. 3 is a drawing illustrating the structures of sesquiterpenes of α-barbatene, thujopsene, and β-chamigrene in an unsaturated fuel and hydrogenated species in the saturated fuel mixtures according to embodiments of the invention.
Figure 3:
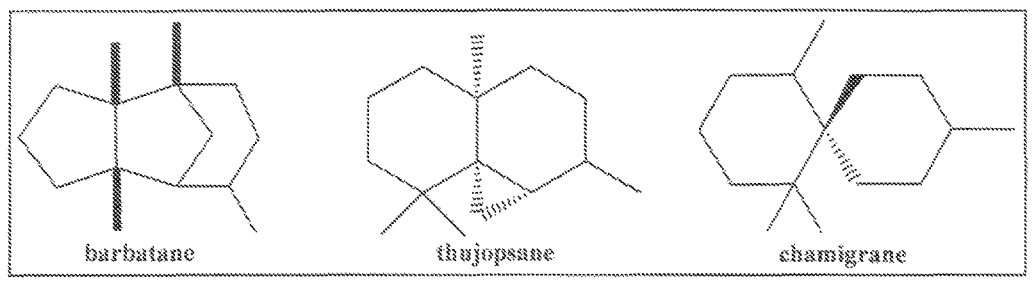

FIG. 3 is a flow diagram illustrating the structures of sesquiterpenes in the unsaturated and saturated fuel mixtures, according to embodiments of the invention.

Fuels based on santalenes have volumetric energy densities greater than JP-5 and F-76 and can be produced from biomass sugars. The range of aircraft and weapon systems is largely dependent on the fuel used for propulsion. Fuels based on santalenes have volumetric net heats of combustion up to ca. 9% higher than conventional Navy jet fuel (JP-5). Moreover, santalenes can be generated from sustainable biomass sugars and other substrates via fermentation. Use of these fuels will reduce net carbon emissions while improving the range and loiter time of a variety of Navy platforms.

1. Santalene mixtures are generated via a fermentation process from biomass sugars or natural gas. Alternatively these mixtures can be isolated from a renewable source, or generated by a metabolically engineered plant.

2. The sesquiterpene blend is purified by fractional distillation or used as a mixture of sesquiterpenes.

3. Alternatively, the mixture can be dimerized to yield a mixture rich in C30 hydrocarbons.

4. The product mixture is hydrogenated to yield a saturated mixture.

5. Saturated mixtures are suitable as standalone fuels or blended with other fuels to achieve desired properties. Additives, including cetane enhancers can be added to the reduced sesquiterpenes to generate full-performance jet or diesel fuels. Dimerized mixtures have utility as lubricants.

The following is a description of some of the embodiments of the invention.

1. A mixture of alpha-santalene, beta-santalene, alpha-bergamotene, and farnesene isomers is generated from substrates including biomass sugars or natural gas via a fermentation process. Feedstocks can include cellulose, hemicellulose, glucose, sucrose, other reducing sugars, cellobiose, lignocellulosic materials, lignin, natural gas, and $CO_2$. Alternatively, mixtures of sesquiterpenes including santalenes can be isolated from plant extracts by steam distillation.

2. In embodiments, a mixture comprising >60% santalenes along with additional sesquiterpenes is isolated. In other embodiments, a santalene enriched mixture is isolated by fractional distillation.

3. In embodiments the sesquiterpene mixture is dimerized to generate a lubricant mixture. The mixture can be dimerized thermally or in the presence of a homogenous or heterogeneous catalyst. In embodiments the catalyst is an acid catalyst including zeolites, aluminosilicates, clays, cation exchange resins, etc.

4. Antioxidants including phenolics are added to the unsaturated sesquiterpene mixture to increase the storage stability of the hydrocarbons. In a preferred embodiment, the sesquiterpene mixture is hydrogenated in the presence of a catalyst under a hydrogen atmosphere to obtain a saturated sesquiterpene mixture. In embodiments the hydrogenation is conducted in acetic acid. In embodiments, the unsaturated fuel has a density of 0.89 g/mL, a volumetric net heat of combustion (NHOC) of 136.6 kBtu/gal, a flashpoint of 106° C., a −20° C. dynamic viscosity of 16.2 cP, a 40° C. dynamic viscosity of 2.47 cP, and a glass transition temperature of −93° C. In embodiments, the saturated sesquiterpene mixture has a density of 0.864 g/mL, a volumetric net heat of combustion of 133.1 kBtu/gal, a −20° C. dynamic viscosity of 19.9 cP, a 40° C. dynamic viscosity of 2.6 cP, and a glass transition temperature of −95° C. In other embodiments, either the unsaturated or saturated sesquiterpene mixture is isomerized with an acid catalyst for the purposes of decreasing the viscosity, increasing the density and net heat of combustion, or increasing the cetane number. In embodiments, the product of the isomerization reaction includes a diamondoid structure. In embodiments the isomerized mixture is purified by fractional distillation.

5. Fuel mixtures including unsaturated sesquiterpene blends and saturated sesquiterpene blends are combined with other renewable or petroleum-based fuels. In embodiments the sesquiterpene/pane fuels are blended with Jet-A, JP-8, JP-5, JP-10, RJ-4, F-76, commercial diesel fuel. In other embodiments, the sesquiterpene/pane fuels are blended with high cetane fuels derived via a Fischer-Tropsch process or Alcohol-to-Jet (ATJ) process to generate fuels with cetane numbers in the range of 30-50 . In other embodiments the sesquiterpene fuels are blended with nitrate esters or other cetane enhancers in low concentration to yield fuels with increased cetane numbers.

Embodiments of the invention generally relate to methods for manufacturing turbine and diesel fuels including, providing a sesquiterpene mixture having santalene(s), and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation, purifying the sesquiterpene mixture to produce pure santalenes or pure sesquiterpene mixtures, isomerizing the pure santalenes or pure sesquiterpene mixtures with at least one heterogeneous or homogenous acid catalyst to produce isomers, hydrogenating the isomers with at least one hydrogenation catalyst under hydrogen pressure, and distilling the isomers to produce a first high density fuel and a higher molecular weight residue, or further isomerizing the isomers with at least one Lewis acid catalyst to generate a hydrocarbon mixture having adamantanes and distilling the adamantane mixture to produce a second high density fuel mixture and a higher molecular weight residue.

In embodiments, the sesquiterpene mixture has about >60 weight % santalenes. In embodiments, the sesquiterpene mixture has alpha-santalene, beta-santalene, alpha-bergamotene, farnesene, in any proportional combination thereof. In embodiments, the residue obtained after distillation of the first or the second high density fuel is purified by vacuum distillation to yield a lubricant composed primarily of C30 hydrocarbons. In embodiments, the hydrogenating catalyst has at least one metal selected from the group consisting of Ni, Cu, Pd, Pt, and Ru. In embodiments, the heterogeneous or homogenous acid catalyst is selected from the group consisting of at least one of perfluorinated sulfonic acid resins, cross-linked sulfonic acid resins, acid clays, zeolites, polyphosphoric acid, cation exchange resins, Lewis acid catalysts, supported Brnsted acid catalysts, mineral acids including $H_2SO_4$ and $H_3PO_4$, and any mixtures thereof.

In embodiments, the Lewis acid catalyst is selected from $AlCl_3$, $AlBr_3$, $AlI_3$, Lewis acidic ionic liquids, $BF_3$, gallium triflate, indium triflate, other strong Lewis acids, and any combination thereof. In embodiments, the first or second high density fuel has a density between 0.86 and 0.92 g/mL and a volumetric net heat of combustion >130,000 btu/gal. In embodiments, the first high density fuel or the second high density fuel mixture is blended with cetane enhancers including alkyl nitrates to generate fuels with cetane numbers >40. In embodiments, the first high density fuel or the second high density fuel mixture has a viscosity between about 15 and 60 cP at −20° C. In embodiments, the first high density fuel or the second high density fuel mixture has a viscosity <4 cP at 40° C.

In embodiments, the first high density fuel or the second high density fuel mixture is blended with petroleum-based fuels including JP-10, RJ-4, JP-8, JP-5, F-76, Diesel #2, and Jet A. In embodiments, the first high density fuel or the second high density fuel mixture is blended with a high cetane blendstock including fuels generated via a Fischer-Tropsch process, ethylene oligomerization, butene oligomerization, hexene oligomerization, to generate fuels with cetane numbers >40. In embodiments, the lubricant has a viscosity >20 cP at 40° C. In embodiments, the purified sesquiterpene mixtures are combined with antioxidants including BHT, and/or renewable phenols, and used as fuels without hydrogenation.

Another aspect of the invention generally relates to the fuels produced by the methods herein. Another aspect of the invention generally relates to methods for manufacturing turbine and diesel fuels including, providing a sesquiterpene mixture having santalene(s), and generated by metabolically engineered organisms from substrates including glucose, sucrose, fructose, other reducing sugars, cellobiose, cellulose, hemicellulose, lignocellulose, lignin, methane, natural gas, and $CO_2$, or isolated from plant material by solvent extraction or steam distillation, purifying the sesquiterpene mixture to produce pure santalene or pure sesquiterpene mixtures, and hydrogenating the pure santalene or pure sesquiterpene mixture with at least one hydrogenation catalyst under hydrogen pressure, and distilling the isomers to produce a high density fuel.

Figure 4:
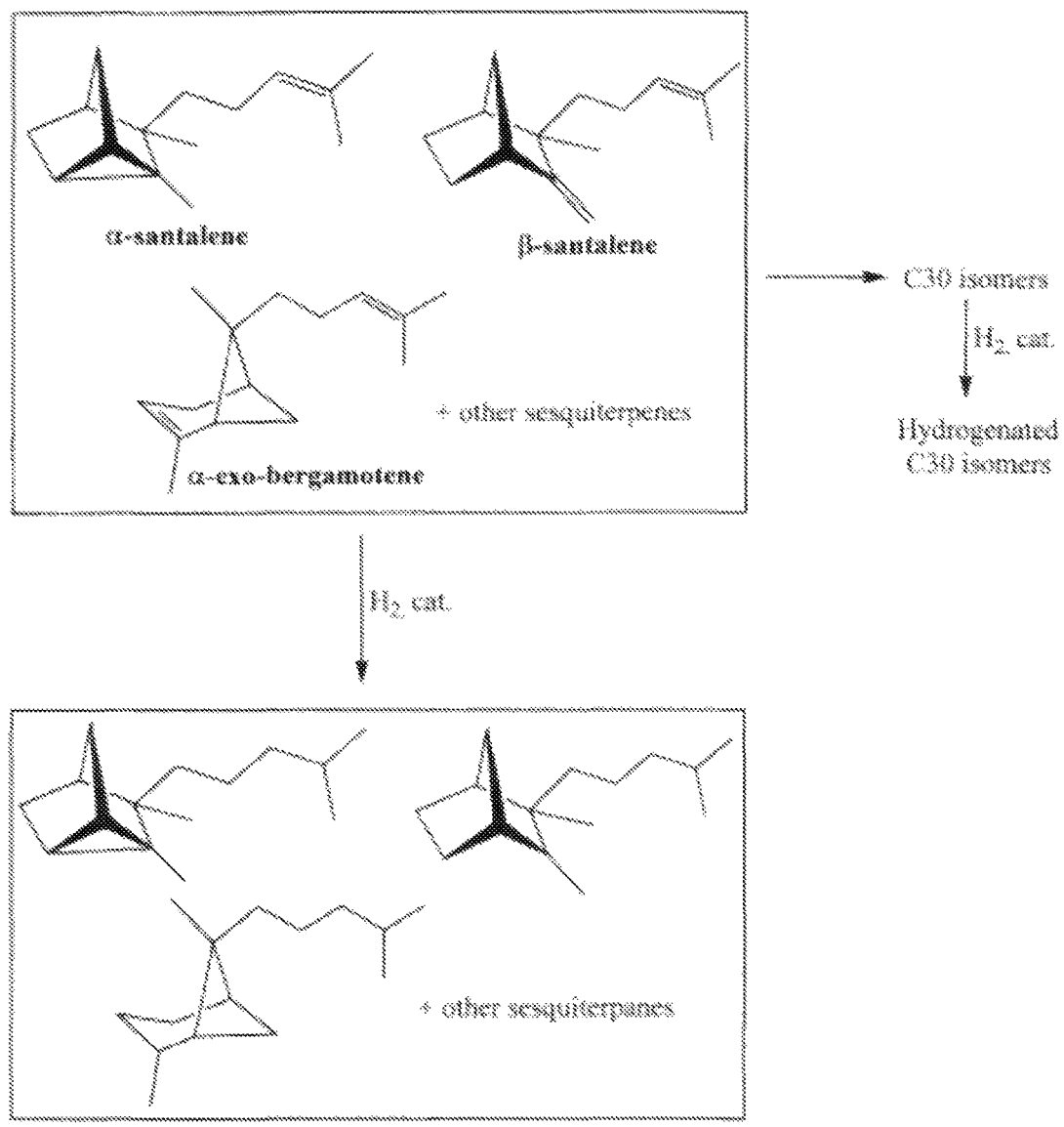
FIG. 4 is a flow diagram illustrating the preparation of fuels and lubricants from santalene-rich sesquiterpene mixtures, according to embodiments of the invention.

FIG. 4 is a flow diagram illustrating the preparation of fuels and lubricants from santalene-rich sesquiterpene mixtures, according to embodiments of the invention.

The range of aircraft and weapon systems is largely dependent on the fuel used for propulsion. Fuels based on ziza-anes have volumetric net heats of combustion up to ca. 18% higher than conventional Navy jet fuel (JP-5). Moreover, ziza-anes can be generated from sustainable biomass sugars via fermentation. Use of these fuels will reduce net carbon emissions while improving the range and loiter time of a variety of Navy platforms.

1. zizaene or isozizaene mixtures are generated via a fermentation process from biomass sugars or natural gas. Alternatively these sesquiterpene mixtures can be isolated from a renewable source, or generated by a metabolically engineered plant.

2. The sesquiterpene blend is purified by fractional distillation or used as a mixture of sesquiterpenes.

3. Alternatively, the mixture can be dimerized to yield a mixture rich in C30 hydrocarbons.

4. The product mixture is hydrogenated to generate zizaane mixtures.

5. Saturated mixtures are suitable as standalone fuels or blended with other fuels to achieve desired properties. Additives, including cetane enhancers can be added to the reduced sesquiterpenes to generate full-performance jet or diesel fuels. Dimerized mixtures have utility as lubricants.

The following are descriptions of some embodiments of the invention.

1. A mixture of zizaene, prezizaene, and other sesquiterpenes is generated from substrates including biomass sugars or natural gas via a fermentation process. In embodiments, a mixture including isozizaene is generated. Feedstocks can include cellulose, hemicellulose, and lignocellulosic materials. Alternatively, mixtures of sesquiterpenes including zizaene or isozizaene can be isolated from plant extracts by steam distillation.

2. In embodiments, a mixture comprising >75% zizaene along with additional sesquiterpenes is isolated. In other embodiments, a zizaene or isozizaene enriched mixture is isolated by fractional distillation.

3. In embodiments, the sesquiterpene mixture is dimerized to generate a lubricant mixture. The mixture can be dimerized thermally or in the presence of a homogenous or heterogeneous catalyst. In embodiments the catalyst is an acid catalyst including zeolites, aluminosilicates, clays, cation exchange resins, etc.

4. Antioxidants including phenolics are added to the unsaturated sesquiterpene mixture to increase the storage stability of the hydrocarbons. In a preferred embodiment, the sesquiterpene mixture is hydrogenated in the presence of a catalyst under a hydrogen atmosphere to obtain a saturated sesquiterpene mixture. In embodiments the hydrogenation is conducted in acetic acid. In embodiments, the unsaturated fuel has a density of 0.94 g/mL, a volumetric net heat of combustion (NHOC) of 147.4 kBtu/gal, a flashpoint of 98° C., a −20° C. dynamic viscosity of 28.2 cP, a 40° C. dynamic viscosity of 3.93 cP, and a glass transition temperature of −94° C. In embodiments, the saturated sesquiterpene mixture has a density of 0.929 g/mL, a volumetric net heat of combustion of 141.9 kBtu/gal, a −20° C. dynamic viscosity of 42.9 cP, a 40° C. dynamic viscosity of 4.3 cP, and a glass transition temperature of −94° C. In other embodiments, either the unsaturated or saturated sesquiterpene mixture is isomerized with an acid catalyst for the purposes of decreasing the viscosity, increasing the density and net heat of combustion, or increasing the cetane number. In embodiments, the product of the isomerization reaction includes a diamondoid structure. In embodiments the isomerized mixture is purified by fractional distillation.

5. Fuel mixtures including unsaturated sesquiterpene blends and saturated sesquiterpene blends are combined with other renewable or petroleum-based fuels. In embodiments the sesquiterpene fuels are blended with Jet-A, JP-8, JP-5, JP-10, RJ-4, F-76, commercial diesel fuel. In other embodiments, the sesquiterpene/pane fuels are blended with high cetane fuels derived via a Fischer-Tropsch process or Alcohol-to-Jet (ATJ) process to generate fuels with cetane numbers in the range of 30-50. In other embodiments the sesquiterpene/pane fuels are blended with nitrate esters or other cetane enhancers in low concentration to yield fuels with increased cetane numbers.

Embodiments of the invention generally relate to methods for manufacturing turbine and diesel fuels including, providing a sesquiterpene mixture having zizaene(s), and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation, purifying the sesquiterpene mixture to produce pure zizaene or pure sesquiterpene mixtures, isomerizing the pure zizaene or pure sesquiterpene mixtures with at least one heterogeneous or homogenous acid catalyst to produce isomers, hydrogenating the isomers with at least one hydrogenation catalyst under hydrogen pressure; and distilling said isomers to produce a first high density fuel and a higher molecular weight residue, or further isomerizing the isomers with at least one Lewis acid catalyst to generate a hydrocarbon mixture having adamantanes and distilling the adamantine mixture to produce a second high density fuel mixture and a higher molecular weight residue.

In embodiments, the sesquiterpene mixture has >75 weight % zizaene. In embodiments the sesquiterpene mixture has zizaene, prezizaene, isozizaene in any proportional combination thereof. In embodiments, the residue obtained after distillation of the first or the second high density fuel is purified by vacuum distillation to yield a lubricant composed primarily of C30 hydrocarbons. In embodiments, the hydrogenation catalyst has at least one metal selected from the group consisting of Ni, Cu, Pd, Pt, and Ru. In embodiments, the heterogeneous or homogenous acid catalyst is selected from the group consisting of at least one of perfluorinated sulfonic acid resins, cross-linked sulfonic acid resins, acid clays, zeolites, polyphosphoric acid, cation exchange resins, Lewis acid catalysts, supported Brnsted acid catalysts, metal oxides, mineral acids including $H_2SO_4$ and $H_3PO_4$, and any mixtures thereof. In embodiments, the Lewis acid catalyst is selected from $AlCl_3$, $AlBr_3$, $AlI_3$, Lewis acidic ionic liquids, $BF_3$, gallium triflate, indium triflate, and other strong Lewis acids, and any combination thereof.

In embodiments, the first or second high density fuel has a density >0.92 g/mL and a volumetric net heat of combustion >140,000 btu/gal. In embodiments, the first high density fuel or the second high density fuel mixture is blended with cetane enhancers including alkyl nitrates to generate fuels with cetane numbers >40. In embodiments, the first high density fuel or the second high density fuel mixture has a dynamic viscosity between about 25 and 50 cP at −20° C. In embodiments, the first high density fuel or the second high density fuel mixture has a dynamic viscosity <5 cP at 40° C. In embodiments, the first high density fuel or the second high density fuel mixture is blended with petroleum-based fuels including JP-10, RJ-4, JP-8, JP-5, F-76, Diesel #2, and Jet A. In embodiments, the first high density fuel or the second high density fuel mixture is blended with a high cetane blendstock including fuels generated via a Fischer-Tropsch process, ethylene oligomerization, butene oligomerization, or hexene oligomerization, to generate fuels with cetane numbers >40. In embodiments, the lubricant has a dynamic viscosity >20 cP at 40° C. In embodiments, the purified sesquiterpenes are combined with antioxidants including BHT, renewable phenols, and used as fuels without hydrogenation.

Another aspect of the invention generally relates to fuels produced by the methods herein. Another aspect of the invention generally relates to methods for manufacturing turbine and diesel fuels including, providing a sesquiterpene mixture having zizaene, and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation, and purifying the sesquiterpene mixture to produce pure zizaene or sesquiterpene mixtures, hydrogenating the pure zizaene or pure sesquiterpene mixture with at least one hydrogenation catalyst under hydrogen pressure, and distilling the isomers to produce a high density fuel.

Figure 5:
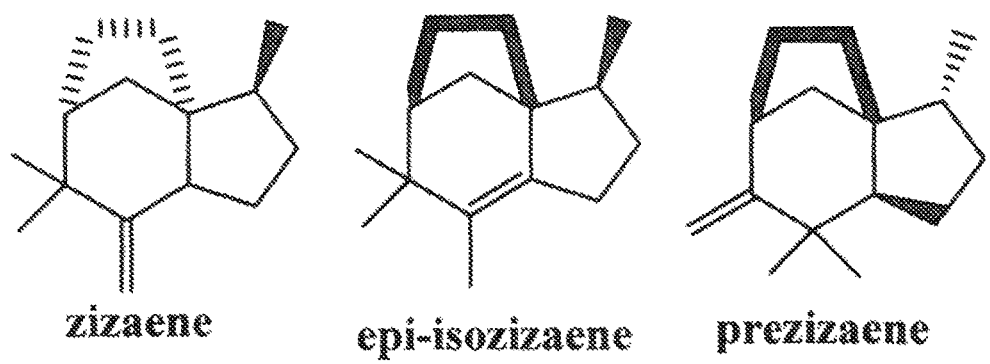
FIG. 5 is a drawing illustrating the structures of zizaene, epi-isozizaene, and prezizaene, according to embodiments of the invention.

FIG. 5 is a flow diagram illustrating sesquiterpene structures, according to embodiments of the invention.

The range of aircraft and weapon systems is largely dependent on the fuel used for propulsion. Fuels based on longifolene have volumetric net heats of combustion up to 17% higher than conventional Navy jet fuel (JP-5). Moreover, longifolene can be generated from sustainable biomass sugars via fermentation. Use of these fuels will reduce net carbon emissions while improving the range and loiter time of a variety of Navy platforms.

1. Longifolene is generated via a fermentation process from biomass sugars or natural gas. Alternatively it is isolated from a renewable source (i.e. tree resin) or generated by a metabolically engineered plant.

2. Longifolene is purified by fractional distillation or used as a mixture of sesquiterpenes.

3. Alternatively, longifolene can be dimerized with or without a catalyst to generate dimers with utility as lubricants.

4. The product mixture is hydrogenated to generate longifolane.

5. Longifolane can be used directly as a fuel or blended with other fuels to achieve desired properties. Additives, including cetane enhancers, can be added to longifolane to generate jet or diesel fuels. Dimerized mixtures have utility as lubricants.

The following are descriptions of some embodiments of the invention.

1. Longifolene is generated from substrates including biomass sugars or natural gas via a fermentation process. Feedstocks can include cellulose, hemicellulose, and lignocellulosic materials. Alternatively longifolene can be isolated from tree resin by distillation or used as a mixture with other sesquiterpenes.

2. In embodiments, the longifolene is obtained in >95% purity by fractional distillation. In other embodiments the longifolene is obtained in >75% purity along with additional sesquiterpenes including, but not limited to, longipinene, longicyclene, sativene, and cyclosativene.

3. In embodiments longifolene is dimerized to generate a lubricant mixture. Longifolene can be dimerized thermally or in the presence of a homogenous or heterogeneous catalyst. In embodiments the catalyst is an acid catalyst including zeolites, aluminosilicates, clays, cation exchange resins, etc.

4. Antioxidants including phenolics are added to longifolene to increase the storage stability of the hydrocarbon. In a preferred embodiment, longifolene is hydrogenated in the presence of a catalyst under a hydrogen atmosphere to obtain longifolene or a mixture of saturated sesquiterpenes including longifolane. In embodiments the hydrogenation is conducted in acetic acid. In embodiments the unsaturated fuel has a density of 0.94 g/mL at 20° C., a net heat of combustion from >142-kBtu/gal, a flashpoint of 88° C., a −20° C. dynamic viscosity of 53.1 cP, a 40° C. dynamic viscosity of 5.82 cP, and a glass transition temperature of −98° C. In embodiments the hydrogenated hydrocarbon mixture has a density of 0.918 g/mL, a volumetric NHOC of 138-142 kBtu/gal, a −20° C. dynamic viscosity of 70 cP, a 40° C. dynamic viscosity of 6.6 cP, and a glass transition temperature of −97° C. In other embodiments, either longifolene or longifolane is isomerized with an acid catalyst for the purposes of decreasing the viscosity, increasing the density and net heat of combustion, or increasing the cetane number. In embodiments, the product of the isomerization reaction is a diamondoid structure. In embodiments the isomerized mixture is purified by fractional distillation.

5. Fuel mixtures including longifolene, longifolane, isomerized longifolene, isomerized longifolane, longifolene blends, hydrogenated longifolene blends, isomerized longifolene blends, and isomerized longifolane blends are combined with other renewable or petroleum-based fuels. In embodiments the sesquiterpene/pane fuels are blended with Jet-A, JP-8, JP-5, JP-10, RJ-4, F-76, commercial diesel fuel. In other embodiments, the sesquiterpene/pane fuels are blended with high cetane fuels derived via a Fischer-Tropsch process or Alcohol to-Jet (ATJ) process to generate fuels with cetane numbers in the range of 30-50. In other embodiments the sesquiterpene fuels are blended with nitrate esters or other cetane enhancers in low concentration to yield fuels with increased cetane numbers.

Embodiments of the invention generally relate to methods for manufacturing turbine and diesel fuels including, providing a sesquiterpene mixture having longifolene, and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation, purifying the sesquiterpene mixture to produce pure longifolene or sesquiterpene mixtures, isomerizing the pure longifolene or pure sesquiterpene mixtures with a heterogeneous or homogenous acid catalyst to produce isomers, hydrogenating the isomers with at least one hydrogenation catalyst under hydrogen pressure, and distilling the isomers to produce a first high density fuel and a higher molecular weight residue, or further isomerizing the isomers with at least one Lewis acid catalyst to generate a hydrocarbon mixture having adamantanes and distilling the adamantane mixture to produce a second high density fuel mixture and a higher molecular weight residue.

In embodiments, the sesquiterpene mixture has >95 weight % longifolene. In embodiments, the sesquiterpene mixture has longifolene, longipinene, longicyclene, sativene, and cyclosativene in any proportional combination. In embodiments, the residue obtained after distillation of the first or the second high density fuel mixture is purified by vacuum distillation to yield a lubricant composed primarily of C30 hydrocarbons. In embodiments, the hydrogenation catalyst having at least one metal selected from the group consisting of Ni, Cu, Pd, Pt, and Ru. In embodiments, the heterogeneous or homogenous acid catalyst is selected from the group consisting of at least one of perfluorinated sulfonic acid resins, cross-linked sulfonic acid resins, acid clays, zeolites, polyphosphoric acid, cation exchange resins, Lewis acid catalysts, supported Brnsted acid catalysts, mineral acids including $H_2SO_4$ and $H_3PO_4$, and any mixtures thereof. In embodiments, the Lewis acid catalyst is selected from the group consisting of $AlCl_3$, $AlBr_3$, $AlI_3$, Lewis acidic ionic liquids, $BF_3$, gallium triflate, indium triflate, and other strong Lewis acids, and any combination thereof.

In embodiments, the first or second high density fuel has a density >0.91 g/mL and a volumetric net heat of combustion >138,000 btu/gal. In embodiments, the first high density fuel or the second high density fuel mixture is blended with cetane enhancers including alkyl nitrates to generate fuels with cetane numbers >40. In embodiments, the first high density fuel or the second high density fuel mixture has a dynamic viscosity between about 40 and 70 cP at −20° C. In embodiments, the first high density fuel or the second high density fuel mixture has a dynamic viscosity <6 cP at 40° C. In embodiments, the first high density fuel or the second high density fuel mixture is blended with petroleum-based fuels including JP-10, RJ-4, JP-8, JP-5, F-76, Diesel #2, and Jet A.

In embodiments, the first high density fuel or the second high density fuel mixture is blended with a high cetane blendstock including fuels generated via a Fischer-Tropsch process, ethylene oligomerization, butene oligomerization, hexene oligomerization, to generate fuels with cetane numbers >40. In embodiments, the lubricant has a dynamic viscosity >20 cP at 40° C. In embodiments, the purified sesquiterpenes are combined with antioxidants including BHT, and/or renewable phenols, and used as fuels without hydrogenation. Another aspect of the invention generally relates to fuels produced by the methods herein. Another aspect of the invention generally relates to methods for manufacturing turbine and diesel fuels including, providing a sesquiterpene mixture having longifolene, and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation, purifying the sesquiterpene mixture to produce pure longifolene or pure sesquiterpene mixtures, and hydrogenating the pure longifolene or pure sesquiterpene mixture with at least one hydrogenation catalyst under hydrogen pressure; and distilling the isomers to produce a high density fuel.

Figure 6:
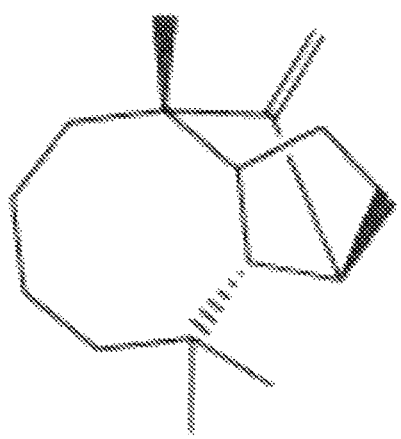
FIG. 6 is a drawing illustrating structures of longifolene and longifolane, according to embodiments of the invention.
Figure 6:
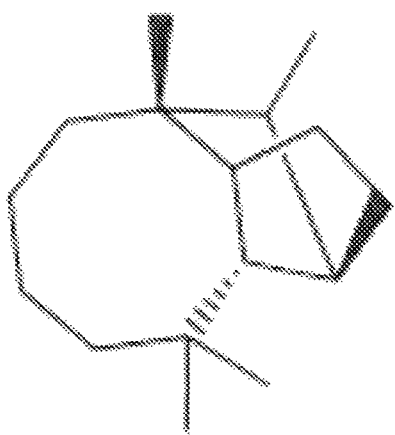

FIG. 6 is a flow diagram illustrating structures of longifolene and longifolane, according to embodiments of the invention.

Embodiments of the invention generally relate to methods for the preparation of renewable fuel blends that have both high density and high cetane numbers. These fuels will reduce the carbon footprint of the Navy while increasing the range and/or loiter time of a variety of Navy platforms. The high cetane number of these fuels allows for their direct use in diesel engines.

This invention describes methods to prepare diesel and jet fuels with densities greater than conventional petroleum-derived fuels while maintaining cetane numbers that allow for combustion in diesel engines. The volumetric energy density of a hydrocarbon fuel is directly related to the gravimetric density. This disclosure describes the preparation of new high performance fuels by blending multicyclic renewable hydrocarbons with synthetic paraffinic kerosenes (SPK). The multicyclic hydrocarbons increase the density and volumetric net heat of combustion of the blend, while the SPK increases the cetane number of the fuels and decreases the viscosity. Through this approach, renewable fuels can be prepared that meet the performance parameters of military grade fuels (i.e. JP-5, JP-8, F-76), while improving the volumetric net heat of combustion. This will result in renewable fuels with the potential to increase the range and/or loiter time of a variety of Navy platforms.

The synthesis of SPKs from ethanol with exceptional cetane numbers is described in related patent application Ser. No. 13/951040 filed on Jul. 25, 2013. The synthesis of SPKs from n-butanol with cetane numbers greater than 50 is described in a number of patents currently issued to the Navy or pending. High density multicyclic fuels based on monoterpenes, sesquiterpenes, diterpenes, adamantanes, and other structures are described in a number of patents currently issued to the Navy or pending. Blends of decalin with SPKs are described in Heyne, J. S.; Boehman, A. L.; Kirby, S. Energy Fuels 2009, 23, 5879-5885.

1. An SPK with a cetane number>about 50 is synthesized from a renewable or petroleum-derived source.

2. A multicyclic hydrocarbon is synthesized from a renewable or petroleum-derived source.

3. Blends of the components generated in 1 and 2 are combined in different ratios to produce fuels that meet the specifications for military grade jet and diesel fuels, while simultaneously increasing the density and volumetric net heat of combustion compared to conventional fuels.

1. SPKs with high cetane numbers can be generated from a variety of sources. In embodiments the SPK is generated by dehydration of an alcohol to an alkene followed by oligomerization. In embodiments the SPK is generated from plant-based oils by decarboxylation and hydrocracking. In embodiments the SPK is generated from sources including biomass and coal via Fischer-Tropsch catalysis. In embodiments the SPK is generated from algal oil. Suitable SPKs contain relatively long hydrocarbon chains with minimal branching. In embodiments, the SPK has a cetane number >50. In embodiments the SPK has a low temperature viscosity <8.0 cSt at −20° C. In embodiments the SPK has a low temperature viscosity <8.5 cSt at −20° C. In embodiments the SPK has a 40 degree C. viscosity between 2.1 and 4.1 cSt.

2. Multicyclic hydrocarbons can be derived from a variety of sources including terpenes, sesquiterpenes, and diterpenes. In embodiments the multicyclic hydrocarbon is generated by cycloaddition of renewable ketones or aldehydes. In embodiments the multicyclic hydrocarbon is generated by cycloaddition of alkenes derived from renewable sources. In embodiments the multicyclic hydrocarbon is decalin. In embodiments the multicyclic hydrocarbon contains an adamantane core. In embodiments the multicyclic hydrocarbon is prepared from norbomadiene. In embodiments the multicyclic hydrocarbon is prepared from cyclopentadiene or a functionalized cyclopentadiene. In embodiments the multicyclic hydrocarbon is prepared from cyclooctatetraene.

In embodiments the multicyclic hydrocarbon is isomerized to increase its cetane number and/or decrease its viscosity prior to blending. In embodiments complex mixtures of multi cyclic hydrocarbons are used. In embodiments a complex mixture is purified by distillation to isolate a pure multicyclic hydrocarbon or preferred mixture of hydrocarbons with increased cetane numbers and/or decreased viscosity.

3. Blends that contain both an SPK and a multicyclic hydrocarbon are prepared. In embodiments, renewable jet fuels with viscosities lower than 8.0 cSt at −20° C. are prepared. In embodiments blends with −20° C. viscosities below 8.5 cSt are prepared. In embodiments blends with cetane numbers greater than 42 are prepared. In embodiments, blends with net heats of combustion>130,000 btu/gal are prepared. In embodiments, blends with densities >0.84 g/mL are prepared. In embodiments mixtures are prepared that include 0-2% aromatic compounds. In embodiments mixtures are prepared that include between 8 and 25% aromatic compounds. The components of the fuel blends studied in this work can be generated from biomass sugars by a combination of fermentation and chemical catalysis which may allow for their production at industrially relevant scales. Despite the abundance of gasoline-powered motor vehicles in the US, diesel is the workhorse fuel around the globe and is particularly important for heavy trucks and ships. According to the World Bank, worldwide per capita consumption of road sector diesel fuel was 118.8 kg (oil equivalent) in 2011 (http://data.worldbank.org/indicator/IS.ROD.DESL.PC/countries/1W?order=wbapi_data_value_2010%20wbapi_data_value%20wbapi_data_value-first &sort=asc&display=default, accessed Nov. 12, 2014) and a recent study by Exxon suggests that diesel fuel use will exceed that of gasoline by 2020 with demand increasing significantly through 2040. (*The Outlook for Energy: A View to* 2040. Exxon Mobil Cooperation, Irving Tex. 2014, cdn.exxonmobil.com/. . . /Outlook%20For%20Energy/ . . . /2014-Outlook-for-Energy.pdf, accessed Oct. 31, 2014). Diesel engines exhibit 53% higher fuel economy and 27% lower CO2 emissions compared to comparable gasoline engines and the potential to increase efficiency and significantly reduce greenhouse gas emissions are key factors supporting the increased adoption of diesel powered vehicles. The benefits of diesel engines have not gone unnoticed by the US Department of Defense. For example, in an effort to increase the range and loiter time of unmanned aerial vehicles (UAVs), the US military is transitioning many of these platforms to diesel engines.

One of the key requirements of diesel fuel is a high cetane number (>42 in the US). Cetane number directly relates to the ignition delay of a given fuel, with shorter ignition delays leading to higher cetane numbers. In general, low cetane fuels result in higher fuel consumption and increased emissions of unburned hydrocarbons. Longer ignition delays can also result in engine knocking and increased engine wear. The cetane numbers of a variety of hydrocarbons were collected by Murphy et al in 2004.(Murphy, et al. *Compendium of Experimental Cetane Number Data;* National Renewable Energy Laboratory (NREL): Golden, Colo., 2004; NREL/SR-540-36805) Drawing from this work, the cetane numbers of several representative hydrocarbons are listed in Table 3. In general, fuels with long straight chains have high cetane numbers that are proportional to chain length, while highly branched paraffins and aromatics have low cetane numbers. For example, hexadecane, which is used as a standard for diesel engine testing, has a cetane number of 100, while the highly branched 2,2,4,6,6-pentamethylheptane has a cetane number of only 9. Lightly branched hydrocarbons such as 2,5-dimethylundecane can have cetane numbers far in excess of that required for diesel fuel, but the position of the branching can greatly reduce the cetane number as is the case for 4,5-diethyloctane with a cetane number of only 20. Aromatics typically have very low cetane numbers due to their excellent stability to oxidation. This property cannot be mitigated by molecular incorporation of even relatively long alkyl chains. For example n-hexylbenzene only has a cetane number of 26. Common cyclic (napthenic) hydrocarbons often have intermediate cetane numbers and subtle structural differences can have significant impacts on their ignition delays. As an example, the trans-isomer of decalin has a cetane number of only 32, while the cis-isomer has a cetane number ten points higher. (Heyne, et al, *Energy Fuels* 2009, 23, 5879-5885)

Table 3. Cetane Numbers of Selected Hydrocarbons.

TABLE 3

Cetane numbers of selected hydrocarbons

| Hydrocarbon | Formula | Structural Type | CN |
|---|---|---|---|
| n-decane | $C_{10}H_{22}$ | paraffin | 76 |
| n-dodecane | $C_{12}H_{26}$ | paraffin | 80 |
| n-hexadecane | $C_{16}H_{34}$ | paraffin | 100 |
| 2,2,4,6,6-pentamethyl heptane | $C_{12}H_{26}$ | isoparaffin | 9 |
| 4,5-diethyloctane | $C_{12}H_{26}$ | isoparaffin | 20 |
| 2,5-dimethylundecane | $C_{13}H_{28}$ | isoparaffin | 58 |
| 1,3,5-trimethylcyclohexane | $C_9H_{18}$ | naphthene | 31 |
| trans-decalin* | $C_{10}H_{18}$ | naphthene | 32 |
| cis-decalin* | $C_{10}H_{18}$ | naphthene | 42 |
| n-butylcyclohexane | $C12H24$ | naphthene | 36 |
| 1,3-diethylbenzene | $C_{10}H_{14}$ | aromatic | 9 |
| biphenyl | $C_{12}H_{10}$ | aromatic | 21 |
| n-hexylbenzene | $C_{12}H_{18}$ | aromatic | 26 |

All of the cetane number except those marked with an * were takan from reference 8.
*See reference 13

The target of most research for the development of full-performance renewable fuels for jet and diesel propulsion has focused on the generation of synthetic paraffinic kerosene (SPK) fuels. These fuels have a number of characteristics that make them attractive for use in both diesel and turbine engines. SPKs burn cleanly and generate little in the way of coke or polyaromatics due to the absence of aromatic compounds in the fuel. The lack of aromatics and cycloalkanes (napthenes) also has a negative impact, evidenced by the decreased density of the fuel. Napthenes typically account for ~35% of JP-5 (high flashpoint Navy jet fuel) and JP-8, while aromatics are around 20%. This combination of hydrocarbons results in fuels with densities of ca. 0.81 g/ml.

In contrast, purely paraffinic or isoparaffinic fuels in the C10-C14 range have densities from about 0.73-0.76 g/mL, while renewable diesel range hydrocarbons with their average higher molecular weight have densities of up to 0.78 g/mL. A potential solution to the low density of these fuels is to blend high density cyclic hydrocarbons with the paraffins. One particularly compelling source of renewable cyclic hydrocarbons are terpenoids that can be isolated from pine resin or generated via biosynthetic approaches. Toward this end a number of researchers have been investigating bio-derived cyclic hydrocarbons based on monoterpenes, as fuels. Some of these molecules have densities as high as 0.94 g/ml, with their viscosities dependent on their structures and molecular weight.

To overcome the density limitations of renewable SPKs, this paper explores the utility of dense terpenoid hydrocarbons as blendstocks for the preparation of 100% bio-derived high density diesel fuels. The results of this study are then used to prepare renewable fuel blends that have densities and net heats of combustion higher than petroleum-based fuels while maintaining cetane numbers high enough for use in diesel engines.

Experimental:

JP-10 (exo-tetrahydrodicyclopentadiene) and RJ-4 (exo-dimethyltetrahydrodicylopentadiene) were obtained from the fuel supply depot at the China Lake Naval Air Warfare Center and filtered before use. 5-methylundecane was prepared from 1-hexene as previously described (Harvey 2014) and include ca. 5% 5-methyl-7butyltridecane. A mixture of hydrogenated caryophyllene isomers was prepared from commercial caryophyllene by isomerization and hydrogenation as described in a recent paper. (Harvey, B. G.; Meylemans, H. A.; Gough, R. V.; Quintana, R. L.; Garrison, M. D.; Bruno, T. J. *Phys Chem Chem Phys* 2014, 16, 9448-9457) To increase the cetane number of the caryophyllene mixture, a low catalyst loading (0.4 g Nafion SAC-13/100 ml of —caryophyllene) was utilized. Terpene dimer fuel (TDF), limonene dimer, (Harvey, B. G.; Wright, M. E.; Quintana, R. L. *Energy Fuels* 2010, 24, 267-273; Meylemans, H. A.; Quintana, R. L.; Harvey, B. G. *Fuel* 2012, 97, 560-568) and pinane (Meylemans, H. A.; Baldwin, L. C.; Harvey, B. G. *Energy Fuels* 2013, 27, 883-888) were prepared as previously described. Blends of 5-methylundecane and hydrogenated caryophyllene isomers were prepared by volume. The solutions were then rigorously stirred for ten minutes and allowed to settle before further studies were conducted. Cetane numbers were determined by IQT analysis conducted at Southwest Research Institute using ASTM D6890. Flashpoints were determined by ASTM D7094 on a Grabner Instruments Miniflash FLP. Viscosity measurements were obtained as previously described. (Meylemans, H. A.; Baldwin, L. C.; Harvey, B. G. *Energy Fuels* 2013, 27, 883-888) Densities of the hydrocarbon mixtures at non-ambient conditions were calculated using a volumetric temperature expansion coefficient of 0.00099/° C. Elemental analysis was performed by Atlantic Microlabs, Norcross Ga.

Hydrogenation of Limonene. $PtO_2$ (500 mg, 2.2 mmol) was added to limonene (200 ml, 1.23 mol) in a glass bomb. The atmosphere was exchanged with hydrogen three times via pump/pressurize cycles and the pressure then increased to 40 psi. The reaction flask was then shaken for 36 h at ambient temperature and the catalyst removed by filtration.

Heat of Combustion Studies. A monolith of high purity benzoic acid was cut into cylinders weighing approximately 80 mg. A cylinder was then placed in a platinum capsule, accurately weighed, and then several drops of a given fuel (~30-50 mg) were added to the monolith. The fuel was allowed to soak into the monolith, the sample reweighed, and then the capsule was transferred to a Parr 6725 Semi-Micro calorimeter. After combustion of the sample under 25-30 atm of $O_2$, the net heat of combustion was calculated by subtracting the contribution due to the benzoic acid from the gross heat of combustion and taking into consideration the hydrogen content (determined by EA) and the density of the fuel. NHOC measurements were taken in triplicate and averaged.

Results and Discussion: As a first step to evaluate the potential for developing a renewable high density, high cetane number fuel, it was of interest to determine the cetane number of JP-10 and RJ-4, two high density multicyclic fuels used for missile propulsion (Chemical Schematic 2). JP-10 is essentially pure exo-tetrahydrodicyclopentadiene and the gold standard for high density fuels combining high density (0.935 g/mL), exceptional volumetric net heat of combustion (141,500 btu/gal), a low freezing point (Tm=−79° C.) and excellent low temperature viscosity (8.8 cSt (−20° C.)). RJ-4 or dimethyl-JP-10, has a similar NHOC value, but a slightly higher low temperature viscosity. Recent work has shown that bio-derived RJ-4 can be synthesized from the terpene alcohol linalool. RJ-4 produced in this manner would then be a candidate as a renewable high density blendstock. Both of the fuels were subjected to IQT analysis in order to derive cetane numbers. The tricyclic nature of JP-10 and RJ-4 resulted in poor cetane numbers of 20.4 and 23.5, respectively. This result is not surprising given that JP-10 has four tertiary centers and RJ-4 has six. In light of their very modest cetane numbers, these synthetic hydrocarbons were not considered further as significant components of high density diesel fuels.

After establishing a baseline, the derived cetane numbers of several renewable napthenes including TDF, pinane, hydrogenated limonene dimers, and limonane were measured (Table 4). TDF, which is generated by heterogeneous acid-catalyzed dimerization of gum spirit turpentine, (Meylemans, H. A.; Quintana, R. L.; Harvey, B. G. *Fuel* 2012, 97, 560-568) has recently been the subject of a number of studies. The combustion of TDF blends with JP-10 and pinane have been explored in a shock tube, while the composition of TDF, it's enthalpy of combustion, and its distillation profile have been analyzed via the advanced distillation method.

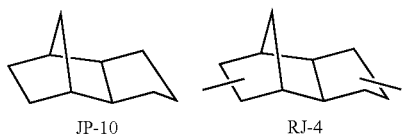

JP-10　　　　　RJ-4

(Chemical Schematic 2). Structures of hydrocarbons present in the high density fuels JP-10 and RJ-4.

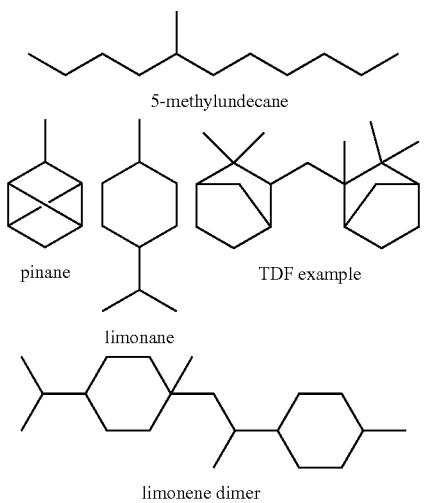

(Chemical Schematic 3.) Structures of some multicyclic and branched chain hydrocarbons studied in this work.

The low temperature viscosity of TDF blended with JP-10, RJ-4, JP-8 and pinane has also been studied.(Meylemans, H. A.; Baldwin, L. C.; Harvey, B. G. *Energy Fuels* 2013, 27, 883-888) TDF contains dimers derived from apinene, camphene, and other terpenes: an example of a typical structure can be found in (Chemical Schematic 3). The mixture of terpene dimers was found to have a moderate cetane number of 27.1. Although the TDF is composed of dozens of isomers, it is known that isomerization of a-pinene prior to dimerization results in the presence of a variety of ring-opened structures. These ring-opened structures, or perhaps formation of hindered tertiary double bonds that are recalcitrant to hydrogenation likely account for the moderate cetane number. In contrast, pinane, a bicyclic molecule that can be generated by hydrogenating a-pinene or 13-pitiene (significant components of pine resin), has three tertiary centers and one quaternary center. This highly branched bicyclic structure resulted in a cetane number of just 23.0.

Table 4. Derived Cetane Numbers of Multicyclic Fuels.

TABLE 4

| Derived cetane numbers of multicyclic fuels | |
|---|---|
| Fuel | Derived Cetane No. |
| Terpene Dimer Fuel | 27.1 |
| JP-10 | 20.4 |
| Hydrogenated α-pinene | 23.0 |
| RJ-4 | 23.5 |
| Hydrogenated Limonene Dimers | 23.1 |
| Limonane | 29.1 |
| Caryophyllane | 24.5 |
| isomerized Caryophyllane | 32.5 |
| 5-methylundecane | 67 |

Hydrogenated limonene (limonane) with three tertiary carbons had a cetane number of 29.1, while dimerization led to a decrease of 6 cetane numbers, perhaps due to formation of new highly substituted carbons or dehydrogenation to yield aromatic structures.

Although this initial set of naphthenic hydrocarbons had low to moderate cetane numbers, it was of interest to evaluate new fuels derived from sesquiterpenes as blendstocks for high density diesel fuels. β-caryophyllene can be isomerized and hydrogenated to a fuel mixture (Chemical Schematic 4) with a density of 0.9 g/ml, net heat of combustion (NHOC) of nearly 138,000 btu/gal, and a cetane number of up to 32.5. Based solely on cetane number, this fuel mixture was the most promising starting point for preparation of a renewable, high density diesel fuel. However, other factors including density, net heat of combustion and low temperature viscosity were also considered. Although TDF has the highest density (0.94 g./mL) and net heat of combustion (142,000 btu/gal) of the renewable napthenes studied in this work, its high viscosity at low temperatures reduces the amount that can be incorporated into a fuel blend. The monoterpanes (limonane and pinane) have substantially lower viscosities, but their modest densities and NHOCs limit their effectiveness as high-density blendstocks. The caryophyllane isomers therefore combine the best properties of the monoterpanes and diterpanes, exhibiting a density and NHOC close to that of TDF, but with a −20° C. viscosity more than two orders of magnitude lower.

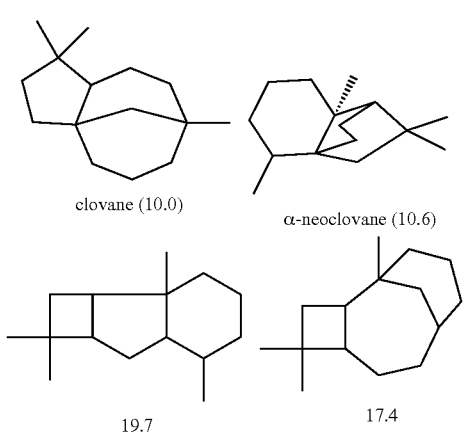

clovane (10.0)　　　α-neoclovane (10.6)

19.7　　　　　17.4

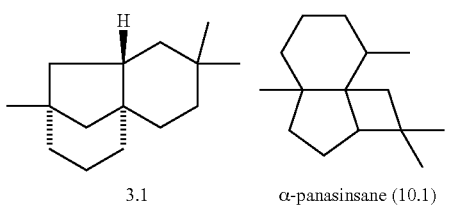

3.1    α-panasinsane (10.1)

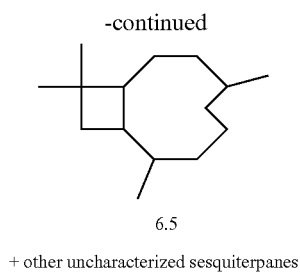

6.5

+ other uncharacterized sesquiterpanes (Chemical Schematic 4.) Structures of sesquiterpanes present in the isomerized mixture. The numbers beneath each structure refer to the area % obtained from GC/MS.

There is some precedence for the idea of using high density napthenes as blendstocks in diesel fuels. For example, the combustion of neat decalin and blends with cyclohexane or hexane have been studied in a diesel engine. (Ogawa, et al, *Energy Fuels* 2007, 21, 1517-1521) In addition, work on JP-900 (a coal based fuel) has shown the utility of blending fuels rich in fused bicyclic hydrocarbons (decalins) with SPK's, biodiesel, or nitrates to generate fuels with high cetane numbers. In a similar manner, blends of a renewable SPK with the caryophyllane isomers would be expected to generate high density fuels with cetane numbers high enough for diesel propulsion. Advantageously we recently developed SPK fuels that can be generated from ethanol via 1-hexene (Chemical Schematic 5). A C12 molecule produced by this approach (5-methylundecane) has a remarkable cetane number of 67 while maintaining excellent low temperature properties. With both the sesquiterpane and branched chain hydrocarbon in hand, it seemed likely that a high density renewable diesel fuel could be created by blending the two components. It was also of interest to generate a fuel with applications as a high density jet fuel.

To achieve these goals three different fuel blends were prepared with different ratios of caryophyllane isomers and 5-methylundecane. The low temperature viscosities of these blends were then measured between −14° C. and 40° C. (FIG. 1). The target was a fuel that would meet the specifications for both JP-5 and F-76, high flashpoint Navy jet and diesel fuel, respectively. In particular, this would require a fuel with an acceptable low temperature viscosity(<8.5 cSt at −20° C.) for jet aircraft, and a suitable high temperature viscosity for diesel applications (>1.7 eSt at 40° C.). The first fuel examined was a 50:50 blend of sesquiterpane isomers and 5-methylundecane. Extrapolation of the viscosity data led to a value of 9.9 cSt at −20° C.

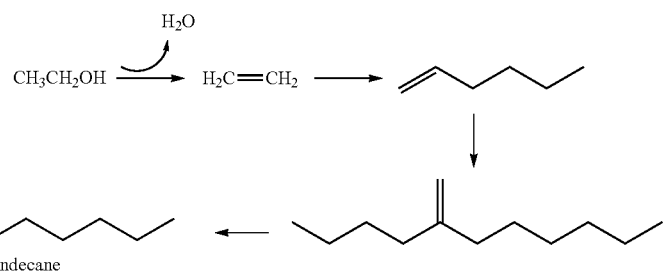

5-methylundecane (Chemical Schematic 5). Synthesis of 5-methylundecane from ethanol.

FIG. 1. Viscosity data for caryophyllane isomers/5-methylundecane blends.

The 40° C. viscosity was 2.5 cSt, well within the viscosity specification for F-76. This fuel could then be considered a potential diesel fuel surrogate and jet fuel blendstock due to its moderate viscosity, while having a density higher than either JP-5 or JP-8 (Table 4). With this result in hand it became of interest to maximize the density while still maintaining a high enough cetane number for use in conventional diesel engines. Using a simple, linear approach and assuming that the cetane number of the sesquiterpane blendstock is ~30, a blend comprised of 65% caryophyllene isomers and 35% hexene dimer was expected to yield a fuel with a cetane number in excess of 42, while maintaining the highest density possible.

TABLE 5

Key properties of renewable fuel blends and conventional petroleum fuels

| Fuel | −20° C. Viscosity (mm$^2$/s) | 40° C. Viscosity (mm$^2$/s) | DCN$^e$ | Density (g/ml) | EA (%) | FP | NHOC (kBtu/gal)$^f$ |
|---|---|---|---|---|---|---|---|
| 65:35 Cl:HD$^a$ | 14.0 | 2.7 | 45.7 (1.1) | 0.853 | C, 86.11; H, 13.89 | 89 | 134.0 (1.6) |
| 50:50 Cl: HD$^a$ | 10.8 | 2.5 | 52.6 (1.1) | 0.826 | C, 85.81; H, 14.13 | 84 | 128.1 (2.2) |
| 40:60 Cl:HD$^a$ | 8.3 | 2.1 | 57.0 (1.1) | 0.806 | C, 85.25; H, 14.29 | 82 | 124.6 (1.5) |
| JP-5$^b$ | <8.5 | NA | ~0.81 | >13.4% H | >60 | ~125 |

TABLE 5-continued

Key properties of renewable fuel blends and conventional petroleum fuels

| Fuel | −20° C. Viscosity (mm²/s) | 40° C. Viscosity (mm²/s) | DCN[e] | Density (g/ml) | EA (%) | FP | NHOC (kBtu/gal)[f] |
|---|---|---|---|---|---|---|---|
| JP-8[c] | <8.0 | NA | | ~0.81 | >13.4% H | >38 | ~125 |
| F-76[d] | NA | 1.7-4.3 | >42 | ~0.84 | >12.5% H | >60 | ~129 |

[a]Cl stands for caryophyllane isomers; HD stands for the hexene dimer (5-methylundecane).
[b]Specifications taken from reference 47.
[c]Specifications taken from reference 49
[d]Specifications takers from reference 48.
[e]Numbers in brackets are the standard deviation for the IQT measurement.
[f]Numbers in brackets are the uncertainty in the measurement.

The cetane number of this blend was 45.7, well within the range for conventional diesel fuel. The blend had an extrapolated viscosity of 13.7 cSt at −20° C. and a 40° C. viscosity of 2.7 cSt with a density of 0.853 g/mL, the final value being higher than conventional F-76.

Although the original 50:50 blend came close to meeting the low temperature viscosity specification for JP-5 (<8.5 cSt at −20° C.), it was of interest to develop a fuel that could meet the viscosity requirement for both JP-5 and JP-8 (<8.0 cSt at −20° C.).47 Preparation of a 40:60 caryophyllene isomer:hexene dimer mixture resulted in a fuel with an extrapolated −20° C. viscosity of 7.9 cSt while maintaining a density of 0.806 g/mL.

To further characterize the fuel blends, the volumetric net heats of combustion were measured. The NHOC varied from 133,593 btu/gal for the highest density fuel to 124,257 btu/gal for the lowest density fuel. These numbers can be compared to F-76 (~129,000 btu/gal) and JP-5 (~N125,000 btu/gal). The NHOC data are quite remarkable for a renewable fuel as evidenced by the fact that the highest density fuel tested in this work has an NHOC approximately 13% higher than conventional biodiesel. (This calculation assumes a NHOC of 118,000 btu/gal for biodiesel).

To further examine the properties of these blends, the amount of hydrogen in the fuels was determined by elemental analysis and the flashpoint of the fuels was measured. Despite the significant concentration of napthenes in the blends, all of the fuels had higher hydrogen contents than required by specifications (Table 4). In addition, the flashpoints of all the fuels were higher than that required by JPS and F-76 (>60° C.) for use onboard Naval vessels.

High density renewable fuel blends include a synthetic paraffinic kerosene combined with a complex multicyclic sesquiterpane mixture have been prepared and characterized. These fuels have excellent cetane numbers and can be formulated to have densities higher than petroleum-derived diesel fuel. The ability to synthesize renewable fuels that outperform petroleum-derived fuels is an emerging trend in biofuel development. Virtually all biofuels are generated via direct biosynthesis or some combination of biosynthesis and chemical catalysis. This provides the opportunity to improve the performance of renewable fuels through custom design of fuel composition. In the current work, both components of the fuel blend can be derived from biomass sugars by combining fermentation processes with chemical catalysis. This suggests that fuels of this type could potentially be generated on a scale that would make them practical for widespread military or commercial use.

Embodiments of the invention generally relate to methods for making a diesel or jet fuel blend including, preparing synthetic paraffinic kerosenes (SPK) and mixing with multicyclic alkanes or alkenes to produce high density diesel fuel blends with cetane numbers >40 or jet fuel blends having low temperature viscosities below 8.5 cSt at −20° C., and where fuel blends having 0.1% to about 25% of at least one aromatic compound. Other aspects of the invention include the fuel blends made by the process or methods herein.

In embodiments, diesel fuel blends have densities greater than about 0.84 g/mL. In embodiments, the jet fuel blends have densities between 0.78 and 0.84 g/mL. In embodiments, the fuel blends have cetane numbers greater than about 42 and the fuel blends have net heats of combustion greater than about 130,000 btu/gal. In embodiments, the fuel blends have 8% to about 25% of at least one aromatic compound.

In embodiments, preparing the SPK is accomplished by dehydrating at least one alcohol to an alkene followed by oligomerization and hydrogenation. In other embodiments, preparing the SPK is accomplished by decarboxylation and hydrocracking of plant-based oils. Yet in other embodiments, preparing the SPK is accomplished by conversion of syngas derived from sources including biomass, natural gas, and coal via use of a Fischer-Tropsch catalysis. Still yet in other embodiments, preparing the SPK is accomplished by decarboxylation and hydrocracking of algal oil.

In embodiments, the SPK includes long chain hydrocarbons having 9-20 carbon atoms with an average of 1-3 chain branches per molecule and the SPK having a cetane number greater than 50. In embodiments, the SPK has a 40° C. viscosity between about 2.1 and about 4.1 cSt. In embodiments, the multicyclic hydrocarbons are prepared from terpenes, sesquiterpenes, and diterpenes. In other embodiments, the multicyclic hydrocarbons are produced by cycloaddition of renewable ketones or aldehydes. In yet other embodiments, the multicyclic hydrocarbons are produced by cycloaddition of alkenes derived from renewable sources.

In embodiments, the multicyclic hydrocarbons are decalin. In embodiments, the multicyclic hydrocarbons include at least one alkyl adamantine. In embodiments, the multicyclic hydrocarbons are prepared from norbornadiene. In embodiments, the multicyclic hydrocarbons are prepared from cyclopentadiene or a functionalized cyclopentadiene. In embodiments, the multicyclic hydrocarbons are prepared from cyclooctatetraene. In embodiments, the multicyclic hydrocarbons are isomerized to increase cetane number and/or decrease viscosity prior to blending. In embodiments, the multicyclic hydrocarbons are a complex mixture of multicyclic sesquiterpanes. In embodiments, the complex mixtures of the multicyclic hydrocarbons are purified by distillation to isolate a pure multicyclic hydrocarbon or mixture of hydrocarbons with increased cetane numbers and/or decreased viscosity. In embodiments, the SPK is 5-methylundecane.

PROPHETIC EXAMPLES

Prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making a diesel fuel blend or a jet fuel blend, comprising:
   (i) cycloaddition of renewable alkenes, ketones, or aldehydes to prepare multicyclic alkanes or multicyclic alkenes, (ii) converting norbornadiene to multicyclic alkanes or multicyclic alkenes, (iii) converting cyclopentadiene or a functionalized cyclopentadiene to multicyclic alkanes or multicyclic alkenes, or (iv) converting cyclooctatetraene to multicyclic alkanes or multicyclic alkenes;
   preparing a synthetic paraffinic kerosene and mixing said synthetic paraffinic kerosene with the multicyclic alkanes or multicyclic alkenes prepared by one of steps (i)-(iv) to produce said deisel fuel blend with a cetane number>40 or said jet fuel blend with a viscosity below 8.5 cSt at −20° C.

2. The method according to claim 1, wherein said diesel fuel blend has a density greater than about 0.84 g/ml and wherein said jet fuel blend has a density between 0.78 g/ml and 0.84 g/ml.

3. The method according to claim 1, wherein said diesel fuel blend or jet fuel blend has a cetane number greater than about 42 and wherein said diesel fuel blend or jet fuel blend has a net heat of combustion greater than about 130,000 btu/gal.

4. The method according to claim 1, wherein said preparing said synthetic paraffinic kerosene is accomplished by dehydrating at least one alcohol to produce an alkene, oligomerizing the alkene to produce an alkene oligomer, and hydrogenating the alkene oligomer to obtain the synthetic paraffinic kerosene.

5. The method according to claim 1, wherein said preparing said synthetic paraffinic kerosene is accomplished by decarboxylation and hydrocracking of plant-based oils.

6. The method according to claim 1, wherein said preparing said synthetic paraffinic kerosene is accomplished by conversion of syngas via use of a Fischer-Tropsch catalyst, wherein said syngas is derived from biomass, natural gas, or coal.

7. The method according to claim 1, wherein said preparing said synthetic paraffinic kerosene is accomplished by decarboxylation and hydrocracking of algal oil.

8. The method according to claim 1, wherein said synthetic paraffinic kerosene comprises long chain hydrocarbons having 9-20 carbon atoms with an average of 1-3 chain branches per hydrocarbon wherein said synthetic paraffinic kerosene has a cetane number greater than 50.

9. The method according to claim 1, wherein said synthetic paraffinic kerosene has a viscosity between about 2.1 cSt and about 4.1 cSt at 40° C.

10. The method according to claim 1, wherein said synthetic paraffinic kerosene is 5-methylundecane.

* * * * *